United States Patent
Tanaka et al.

(10) Patent No.: US 10,238,357 B2
(45) Date of Patent: Mar. 26, 2019

(54) X-RAY CT APPARATUS AND SCANNING METHOD

(71) Applicant: Hitachi, Ltd., Tokyo (JP)

(72) Inventors: Kana Tanaka, Tokyo (JP); Koichi Hirokawa, Tokyo (JP); Yukio Kumagai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 206 days.

(21) Appl. No.: 15/301,299

(22) PCT Filed: Mar. 25, 2015

(86) PCT No.: PCT/JP2015/059031
§ 371 (c)(1),
(2) Date: Sep. 30, 2016

(87) PCT Pub. No.: WO2015/151948
PCT Pub. Date: Oct. 8, 2015

(65) Prior Publication Data
US 2017/0020478 A1  Jan. 26, 2017

(30) Foreign Application Priority Data
Mar. 31, 2014 (JP) ................................ 2014-072054

(51) Int. Cl.
*A61B 6/00* (2006.01)
*A61B 6/02* (2006.01)
(Continued)

(52) U.S. Cl.
CPC .............. *A61B 6/542* (2013.01); *A61B 6/027* (2013.01); *A61B 6/032* (2013.01); *A61B 6/0407* (2013.01);
(Continued)

(58) Field of Classification Search
CPC ......... A61B 6/032; A61B 6/542; A61B 6/488; A61B 6/545
See application file for complete search history.

(56) References Cited

U.S. PATENT DOCUMENTS

| | | |
|---|---|---|
| 6,185,271 B1 | 2/2001 | Kinsinger |
| 2007/0025500 A1* | 2/2007 | Horiuchi .............. G01N 23/046 378/16 |
| 2011/0091008 A1 | 4/2011 | Hirokawa et al. |

FOREIGN PATENT DOCUMENTS

| | | |
|---|---|---|
| CN | 1446517 A | 10/2003 |
| CN | 101128153 A | 2/2008 |

(Continued)

OTHER PUBLICATIONS

International Search Report dated Jun. 30, 2015 for International Patent Application No. PCT/JP2015/059031.

(Continued)

*Primary Examiner* — Dani Fox

(57) ABSTRACT

In order to provide an X-ray CT apparatus and the like capable of obtaining an optimal X-ray dose for a dynamically changing X-ray irradiation region and reliably irradiating the X-ray irradiation region in a case where X-rays are applied with a spreading angle in a body axis direction, an X-ray CT apparatus 1 dynamically changes an X-ray irradiation region 201 for each view angle during scanning, and a system control device 124 changes a position of an analysis line 300 used to calculate an optimal tube current during scanning according to a position of the X-ray irradiation region 201 at each view angle, so as to obtain an optimal irradiation X-ray dose.

17 Claims, 21 Drawing Sheets

(51) Int. Cl.
    *A61B 6/03*           (2006.01)
    *A61B 6/06*           (2006.01)
    *A61B 6/04*           (2006.01)

(52) U.S. Cl.
    CPC .............. *A61B 6/06* (2013.01); *A61B 6/4435* (2013.01); *A61B 6/461* (2013.01); *A61B 6/467* (2013.01); *A61B 6/488* (2013.01); *A61B 6/5205* (2013.01); *A61B 6/545* (2013.01)

(56) References Cited

FOREIGN PATENT DOCUMENTS

| | | |
|---|---|---|
| CN | 102100564 A | 6/2011 |
| JP | 2001145621 A | 5/2001 |
| JP | 2001286459 A | 10/2001 |
| JP | 200720604 A | 2/2007 |
| JP | 2009125250 A | 6/2009 |

OTHER PUBLICATIONS

Chinese Office Action for the Chinese Patent Application No. 201580010291.5, dated Aug. 28, 2018, 8 pages.

\* cited by examiner

FIG.6
(A)
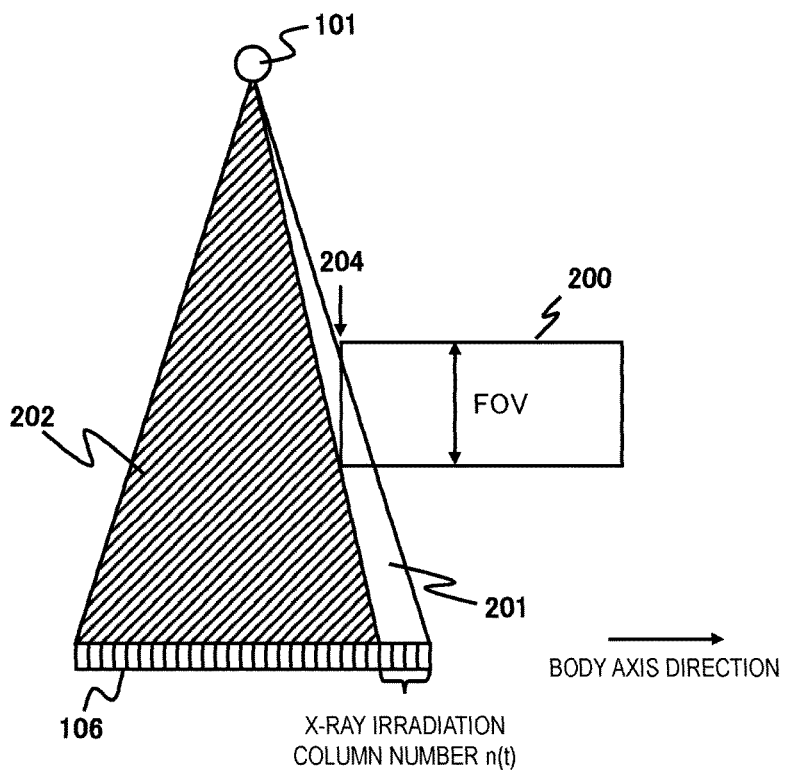
(B)
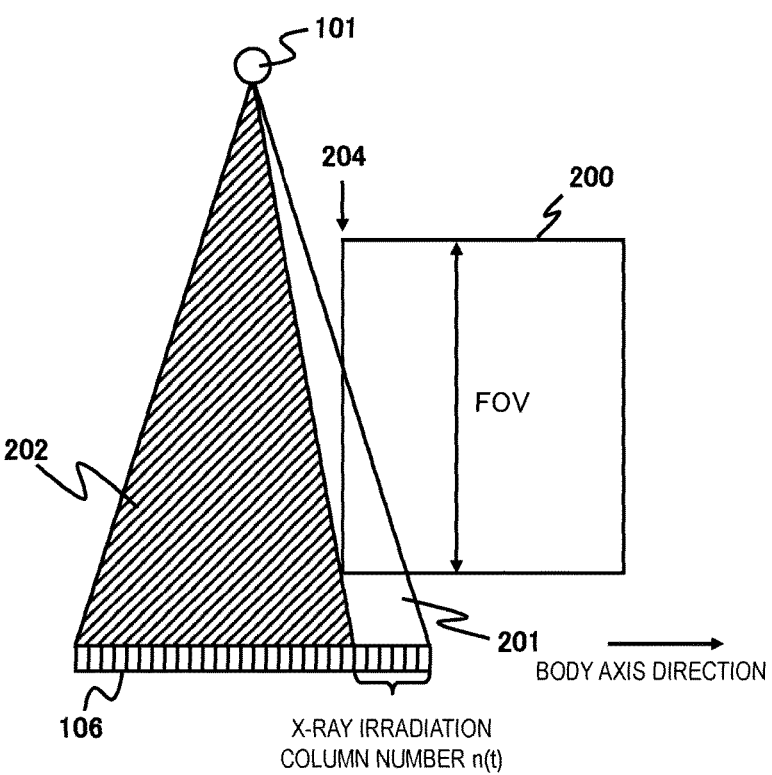

FIG.11
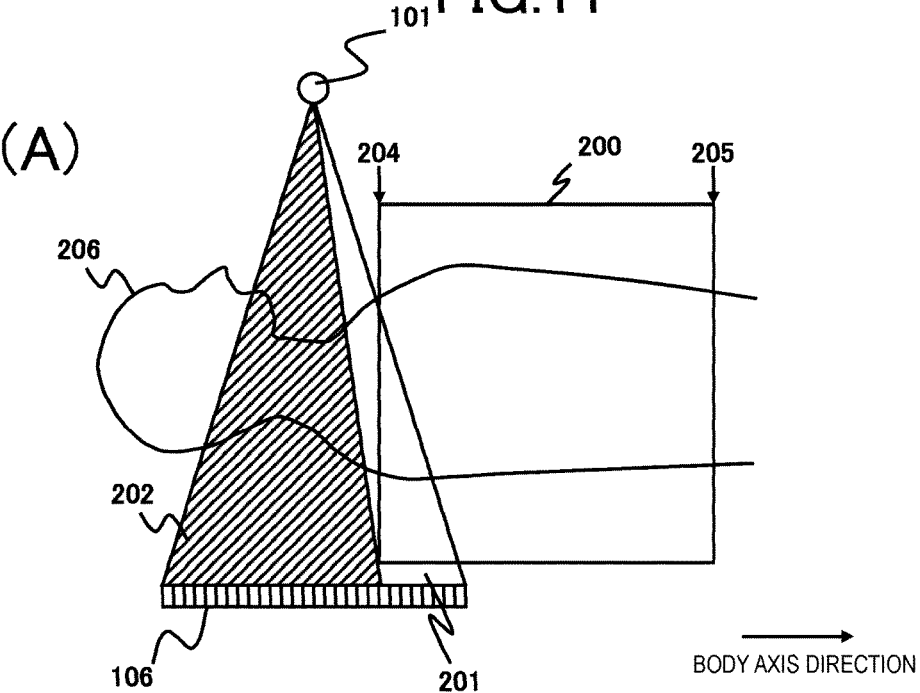
(A)
BODY AXIS DIRECTION
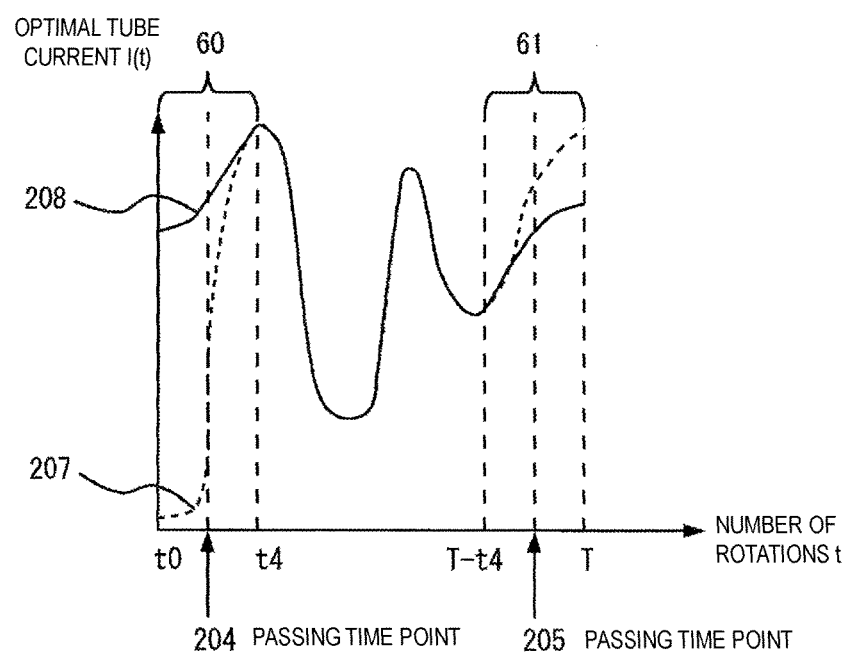
(B)

FIG.12
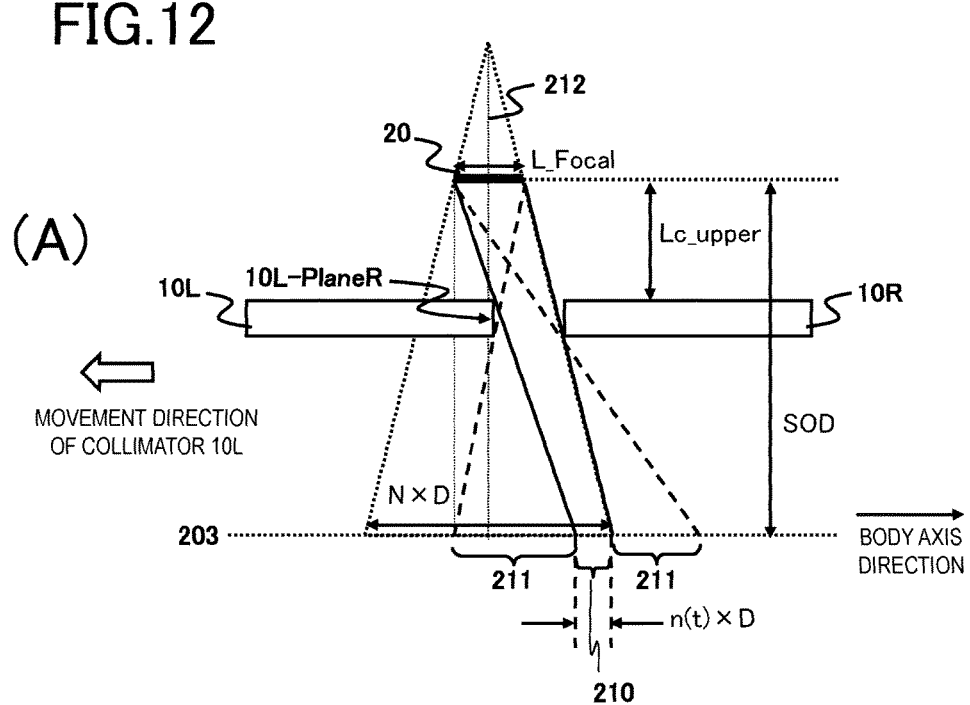
(A)
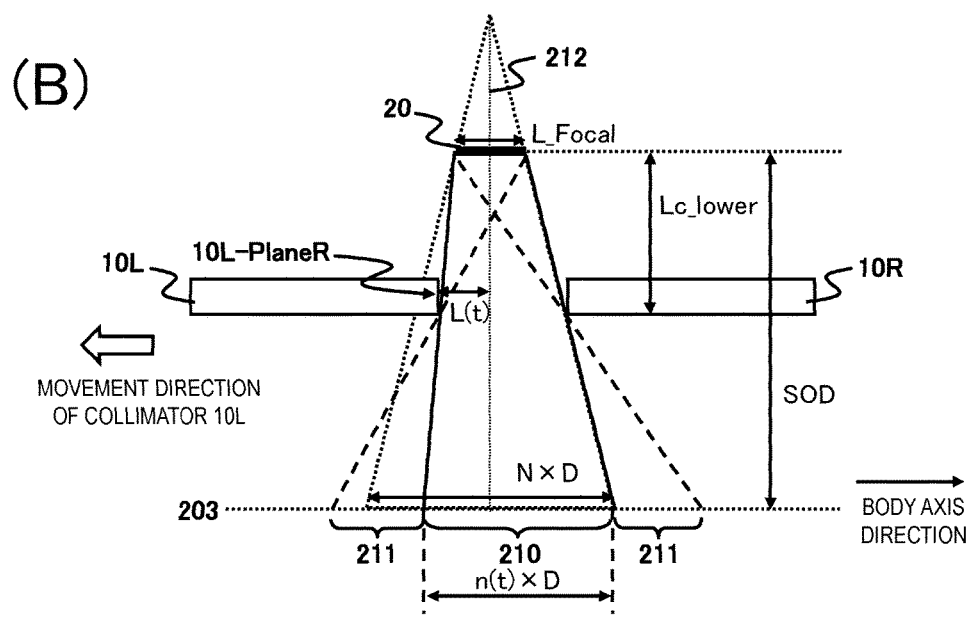
(B)

FIG.19
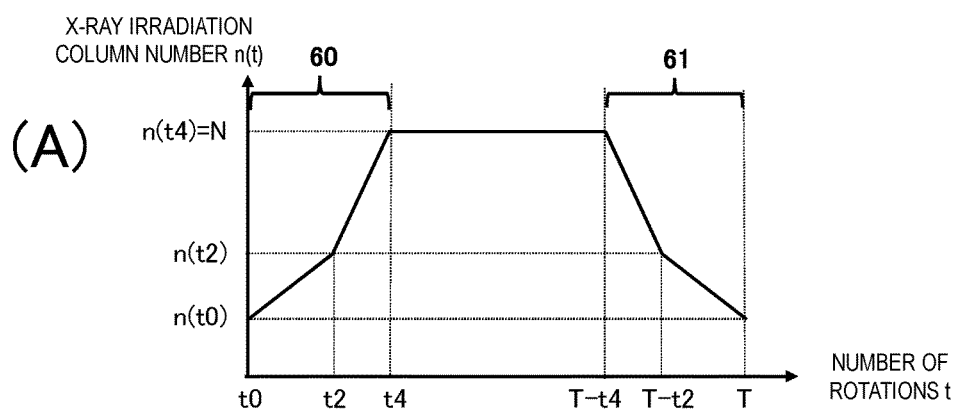
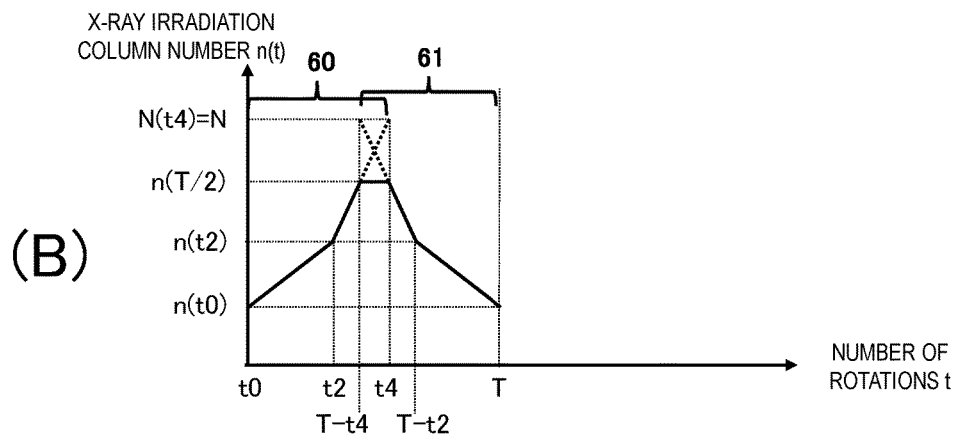

X-RAY CT APPARATUS AND SCANNING METHOD

CROSS-REFERENCE TO RELATED APPLICATIONS

This application is a national phase claiming the benefit of and priority to International Patent Application No. PCT/JP2015/059031, entitled "X-RAY CT DEVICE AND IMAGING METHOD", filed Mar. 25, 2015, which claims priority to Japanese Patent Application No. 2014-072054, entitled "X-RAY CT DEVICE AND IMAGING METHOD", filed Mar. 31, 2014, which are hereby incorporated by reference in their entireties.

TECHNICAL FIELD

The present invention relates to an X-ray CT apparatus and a scanning method, and particularly to optimization of an X-ray dose in a multi-slice CT apparatus.

BACKGROUND ART

An X-ray computed tomography (CT) apparatus is an apparatus which rotates an X-ray source and an X-ray detector around an object in a state of being disposed to oppose each other, applies X-rays from a plurality of rotation angle directions (views), detects X-rays (projection data) transmitted through the object for each view, and generates a tomographic image of the object on the basis of detected projection data. PTL 1 discloses a technique in which a collimator unit is dynamically controlled in the scanning starting vicinity and in the scanning finishing vicinity in a case where helical scanning is performed with a multi-slice CT apparatus (an X-ray CT apparatus provided with multi-column X-ray detectors), and thus only a region of an examination target object substantially used for image reconstruction is irradiated with X-rays so that an exposure dose is reduced.

CITATION LIST

Patent Literature

[PTL 1] JP-A-2001-145621

SUMMARY OF INVENTION

Technical Problem

However, the above-described PTL 1 does not take into consideration an appropriate dose of X-rays applied to an X-ray irradiation region which dynamically changes during scanning. PTL 1 does not take into consideration so-called post-reconstruction in which an image is reconstructed in an image reconstruction condition which is different from a condition set during scanning, and it is not clear how to calculate an X-ray irradiation region. A method of controlling the collimator in order to reliably irradiate the calculated X-ray irradiation region with X-rays is also unclear.

The present invention has been made in consideration of the above-described problems, and an object thereof is to provide an X-ray CT apparatus and the like capable of obtaining an optimal X-ray dose for a dynamically changing X-ray irradiation region and reliably irradiating the X-ray irradiation region in a case where X-rays are applied with a spreading angle in a body axis direction.

Solution to Problem

In order to achieve the above-described object, according to the present invention, there is provided an X-ray CT apparatus including an X-ray source that irradiates an object with X-rays; a collimator that restricts an irradiation range of the X-rays applied from the X-ray source; an X-ray detector that is disposed to oppose the X-ray source and detects X-rays having been transmitted through the object; a rotation board that is mounted with the X-ray source and the X-ray detector and is rotated around the object; a bed that carries the object into and out of an X-ray irradiation region; an image reconstruction device that reconstructs an image of the object on the basis of a transmitted X-ray dose detected by the X-ray detector; a display device that displays the image reconstructed by the image reconstruction device; an X-ray irradiation region calculation unit that calculates an X-ray irradiation region in a body axis direction at each view angle on the basis of an examination condition; an X-ray dose calculation unit that calculates an irradiation X-ray dose at each view angle according to an X-ray irradiation region calculated by the X-ray irradiation region calculation unit; and a control unit that controls scanning so that the irradiation X-ray dose calculated by the X-ray dose calculation unit is applied to the X-ray irradiation region at each view angle calculated by the X-ray irradiation region calculation unit.

There is provided a scanning method including causing a control device of an X-ray CT apparatus to execute processes including a first step of calculating an X-ray irradiation region at each view angle in a body axis direction on the basis of an examination condition; a second step of calculating an irradiation X-ray dose at each view angle according to the X-ray irradiation region calculated in the first step; and a third step of controlling scanning so that the irradiation X-ray dose calculated in the second step is applied to the X-ray irradiation region at each view angle calculated in the first step.

Advantageous Effects of Invention

According to the present invention, it is possible to provide an X-ray CT apparatus and the like capable of obtaining an optimal X-ray dose for a dynamically changing X-ray irradiation region and reliably irradiating the X-ray irradiation region in a case where X-rays are applied with a spreading angle in a body axis direction.

BRIEF DESCRIPTION OF DRAWINGS

FIG. 6 is a diagram for explaining a difference in the X-ray irradiation region 201 due to an FOV.

FIG. 11 is a diagram for explaining effects of the present invention.

FIG. 12 is a diagram for explaining an example of calculating a collimator position corresponding to a collimator thickness.

FIG. 19 is a diagram illustrating temporal changes of an X-ray irradiation region in a comparative manner, in FIG. 19(A) illustrates a case where the number of rotations is large, and FIG. 19(B) illustrates a case where the number of rotations is small.

DESCRIPTION OF EMBODIMENTS

Hereinafter, embodiments of the present invention will be described in detail with reference to the drawings.

First Embodiment

First, with reference to FIG. 1, a description will be made of the entire configuration of an X-ray CT apparatus 1 according to the present invention.

Figure 1:
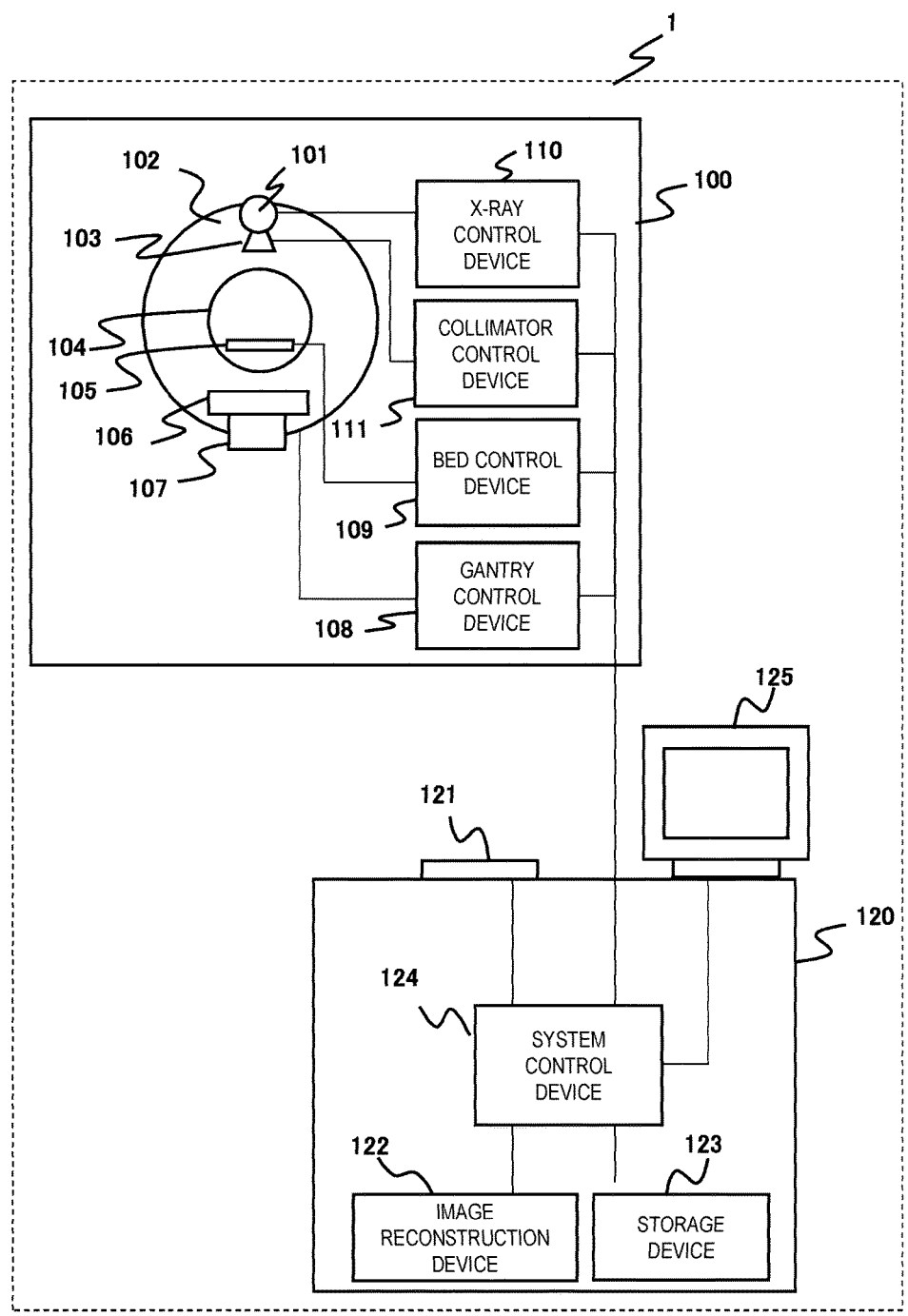
FIG. 1 is the entire configuration diagram of an X-ray CT apparatus 1.

As illustrated in FIG. 1, the X-ray CT apparatus 1 includes a scan gantry portion 100, a bed 105, and an operation console 120. The scan gantry portion 100 is a device which irradiates an object with X-rays and detects X-rays transmitted through the object. The operation console 120 is a device which controls each constituent element of the scan gantry portion 100, and acquires transmitted X-ray data measured by the scan gantry portion 100 so as to generate an image. The bed 105 is a device on which the object is laid and is mounted and which carries the object into and out of an X-ray irradiation range of the scan gantry portion 100.

The scan gantry portion 100 includes an X-ray source 101, a rotation board 102, a collimator unit 103, an X-ray detector 106, a data collecting device 107, a gantry control device 108, a bed control device 109, an X-ray control device 110, and a collimator control device 111.

The operation console 120 includes an input device 121, an image reconstruction device 122, a storage device 123, a system control device 124, and a display device 125.

The rotation board 102 of the scan gantry portion 100 is provided with an opening 104, and the X-ray source 101 and the X-ray detector 106 are disposed to oppose each other with the opening 104 interposed therebetween. An object mounted on the bed 105 is inserted into the opening 104. The rotation board 102 is rotated around the object by a driving force which is transmitted from a rotation board driving device via a driving transmission system. The rotation board driving device is controlled by the gantry control device 108.

The X-ray source 101 is controlled by the X-ray control device 110 so as to apply X-rays with a predetermined intensity continuously or intermittently. The X-ray control device 110 controls an X-ray tube voltage applied to the X-ray source 101 and an X-ray tube current supplied thereto according to an X-ray tube voltage and an X-ray tube current determined by the system control device 124 of the operation console 120.

The collimator unit 103 is provided in an X-ray irradiation outlet of the X-ray source 101. The collimator unit 103 includes a collimator which is a mechanism restricting an irradiation range of X-rays applied from the X-ray source 101, or an X-ray compensation filter which adjusts a dose distribution of X-rays. An operation of the collimator is controlled by the collimator control device 111.

The collimator control device 111 is a device which controls operations of collimators 10, and controls an irradiation range of X-rays applied from the X-ray source 101.

The X-rays, applied from the X-ray source 101, passing through the collimator unit 103, and transmitted through the object, are incident to the X-ray detector 106.

The X-ray detector 106 is a detector in which, for example, about 1000 X-ray detection element groups each constituted of a scintillator and a photodiode are arranged in a rotation direction (channel direction), and, for example, 1 to 320 X-ray detection element groups are arranged in a rotation axis direction (slice direction). The X-ray detector 106 is disposed to oppose the X-ray source 101 via the object. The X-ray detector 106 detects a dose of X-rays applied from the X-ray source 101 and transmitted through the object, and outputs the dose to the data collecting device 107.

The data collecting device 107 collects an X-ray dose detected by each X-ray detection element of the X-ray detector 106, converts the X-ray dose into digital data, and sequentially outputs the digital data to the image reconstruction device 122 of the operation console 120 as transmitted X-ray data.

The image reconstruction device 122 acquires the transmitted X-ray data which is input from the data collecting device 107, and performs pre-processing such as logarithmic conversion and sensitivity correction on the data so as to generate projection data which is necessary in reconstruction. The image reconstruction device 122 reconstructs an image such as a scanogram image or a tomographic image by using the generated projection data. The image reconstruction device 122 generates volume data obtained by stacking reconstructed sliced tomographic images. The system control device 124 displays the projection data, the scanogram image, the tomographic image, and the volume data generated by the image reconstruction device 122 on the display device 125 and also stores the data and the images in the storage device 123.

The system control device 124 is a computer provided with a central processing unit (CPU), a read only memory (ROM), a random access memory (RAM), and the like. The system control device 124 is a device which controls each constituent element of the operation console 120 and the scan gantry portion 100.

Figure 3:
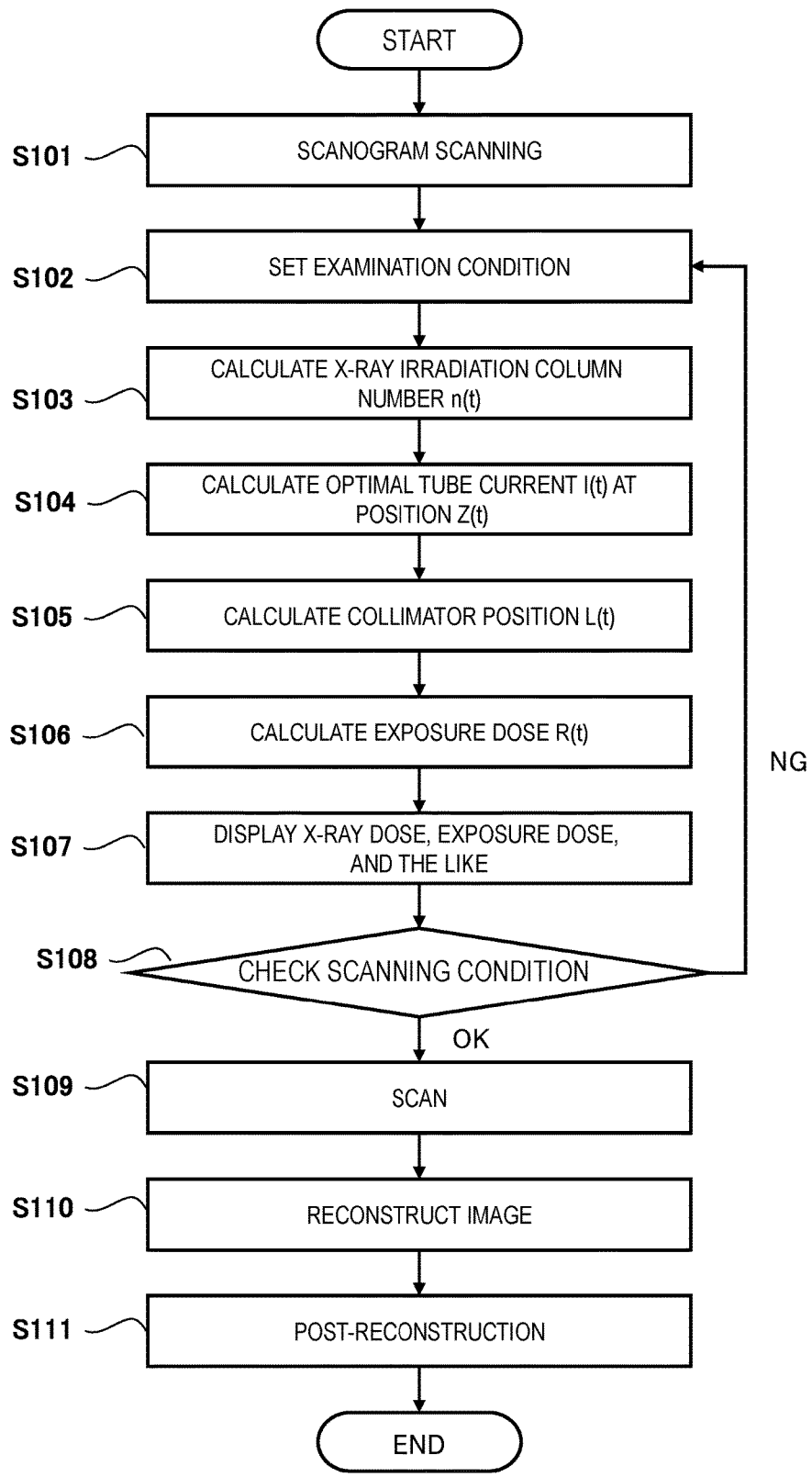
FIG. 3 is a flowchart illustrating the entire flow of a scanning/image reconstruction process performed by the X-ray CT apparatus 1 of a first embodiment.

The system control device 124 performs a scanning/image reconstruction process according to process procedures illustrated in FIG. 3. The scanning/image reconstruction process will be described later in detail.

The storage device 123 is a device storing data collected by the data collecting device 107 and image data created by the image reconstruction device 122, and is, specifically, a data recording device such as a hard disk drive. The storage device 123 stores in advance programs or data for realizing a function of the X-ray CT apparatus 1 in addition to the above-described transmitted X-ray data or image data.

The display device 125 is constituted of a display device such as a liquid crystal panel or a CRT monitor, and a logic circuit for performing a display process in conjunction with the display device, and is connected to the system control device 124. The display device 125 displays an object image output from the image reconstruction device 122, and various information treated by the system control device 124.

The input device 121 is a device for inputting an object name, the examination date and time, an examination condition, and the like, and is constituted of, specifically, a pointing device such as a keyboard or a mouse, and various switch buttons. The input device 121 outputs various instructions or information input by an operator, to the system control device 124. The operator operates the X-ray CT apparatus 1 in an interaction manner by using the display device 125 and the input device 121. The input device 121 may be a touch panel type input device which is integrally formed with a display screen of the display device 125.

Next, with reference to FIG. 2, a functional configuration of the X-ray CT apparatus 1 will be described.

Figure 2:
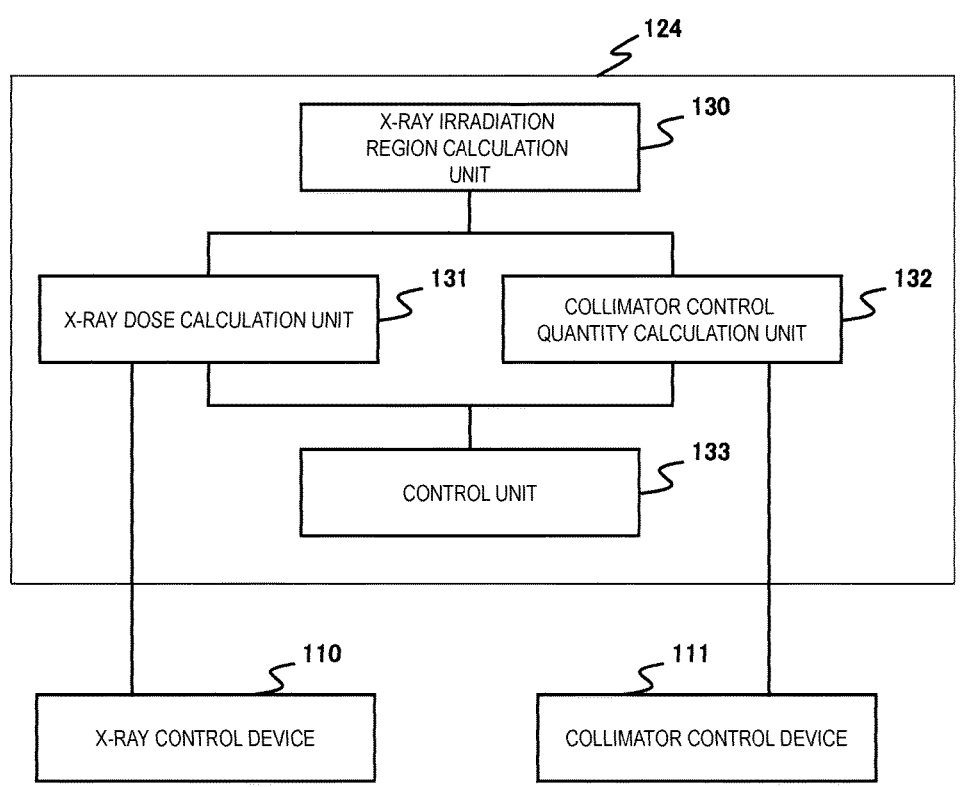
FIG. 2 is a functional configuration diagram of the X-ray CT apparatus 1.

As illustrated in FIG. 2, the system control device 124 of the X-ray CT apparatus 1 of the present invention includes an X-ray irradiation region calculation unit 130, an X-ray dose calculation unit 131, a collimator control quantity calculation unit 132, and a control unit 133.

The X-ray irradiation region calculation unit 130 calculates an X-ray irradiation region in a body axis direction for each view angle on the basis of examination conditions. The examination conditions include scanning conditions and reconstruction conditions, and may be various parameters which are directly input by an operator via the input device 121, and may be determined by the system control device 124. The scanning conditions include parameters such as a beam width, a helical pitch, a tube voltage, and target image noise. The reconstruction conditions include parameters such as a reconstruction filter, a slice thickness, and a field of view (FOV). The reconstruction conditions are assumed to include a "reconstruction condition during scanning" and a post-reconstruction condition. The post-reconstruction condition is a reconstruction condition in which acquired projection data is preserved and is used in the next reconstruction process. The X-ray irradiation region in the body axis direction corresponds to the number of columns (the number of columns in the body axis direction) which is irradiated by X-rays in the multi-column X-ray detector 106. Hereinafter, the X-ray irradiation region in the body axis direction will be referred to as an X-ray irradiation column number n(t) in some cases. The X-ray irradiation region in the body axis direction is calculated for each view, that is, every elapsed time from starting of scanning. This assumes that, for example, the X-ray irradiation column number n(t) in helical scanning is dynamically changed depending on a body axis direction position and a view angle (elapsed time from starting of scanning). In the following description, the helical scanning will be described as a preferred example, but the present invention is applicable to axial scanning.

A notification of the X-ray irradiation region (X-ray irradiation column number) in the body axis direction for each view, calculated by the X-ray irradiation region calculation unit 130, is sent to the X-ray dose calculation unit 131 and the collimator control quantity calculation unit 132.

The X-ray dose calculation unit 131 calculates an irradiation X-ray dose for each view angle according to the X-ray irradiation region in the body axis direction, calculated by the X-ray irradiation region calculation unit 130. In the following description, a tube current value is obtained as the irradiation X-ray dose. A process of calculating an X-ray dose in the X-ray dose calculation unit 131 will be described later in detail. A notification of the X-ray dose (tube current value) calculated by the X-ray dose calculation unit 131 is sent to the X-ray control device 110.

The collimator control quantity calculation unit 132 calculates a control quantity of each of the collimators 10 for applying X-rays to the X-ray irradiation region calculated by the X-ray irradiation region calculation unit 130. Specifically, an X-ray shield region is obtained from the X-ray irradiation region, and control quantities (positions) of the collimators 10 corresponding to the X-ray shield region is calculated. A collimator control quantity calculation process will be described later. A notification of the calculated control quantities (positions) of the collimators 10 is sent to the collimator control device 111. The collimator control device 111 adjusts positions of the collimators 10 on the basis of the collimator control quantity.

The control unit 133 controls scanning so that the irradiation X-ray dose calculated by the X-ray dose calculation unit 131 is applied to the X-ray irradiation region at each view angle, calculated by the X-ray irradiation region calculation unit 130. In other words, an irradiation X-ray dose or positions of the collimators 10 is changed for each view angle according to the X-ray dose (tube current) calculated by the X-ray dose calculation unit 131 and the collimator control quantity calculated by the collimator control quantity calculation unit 132.

The system control device 124 gives an instruction for the X-ray dose (tube current) calculated by the X-ray dose calculation unit 131 to the X-ray control device 110, and gives an instruction for the collimator control quantity calculated by the collimator control quantity calculation unit 132 to the collimator control device 111, so as to cause the control unit 133 to control scanning.

Next, with reference to a flowchart of FIG. 3, a description will be made of a flow of the scanning/image reconstruction process in the X-ray CT apparatus 1.

The system control device 124 of the X-ray CT apparatus 1 performs the scanning/image reconstruction process according to procedures illustrated in the flowchart of FIG. 3. The system control device 124 reads a program and data regarding the scanning/image reconstruction process from the storage device 123, and performs the process on the basis of the program and the data.

In the following description, the helical scanning in multi-slice CT will be described.

(Step S101)

An operator performs scanogram scanning as positioning scanning. In the scanogram scanning, generally, the X-ray source 101 performs irradiation with X-rays with a small beam width at a certain fixed view angle, and projection data of a section which is perpendicular to the bed 105 is collected in the body axis direction. An view angle of the X-ray source 101 is not limited, but there is PA scanogram in which the X-ray source 101 is fixed to a 0-degree direction or a 180-degree direction so that radioscopy is implemented, and LAT scanogram in which the X-ray source is fixed to a 90-degree direction or a 270-degree direction so that radioscopy is implemented.

(Step S102)

The operator sets examination conditions via the input device 121. The examination conditions include an image reconstruction range, a beam width, a helical pitch, a slice thickness, a field of view (FOV), a tube voltage, target image noise, and the like (including scanning conditions and reconstruction conditions).

(Step S103)

The system control device 124 calculates an X-ray irradiation column number n(t) which is necessary in image reconstruction after t rotations from a scanning starting time point on the basis of the scanning conditions set by the operator. Details of the process in step S103 will be described later.

(Step S104)

The system control device 124 calculates an optimal tube current I(t) at a position Z(t) of the X-ray source 101 in the body axis direction after t rotations from the scanning starting time point on the basis of the X-ray irradiation column number n(t) calculated in step S103. Details of the process in step S104 will be described later.

(Step S105)

Collimator positions L(t) (collimator control quantities) in the scanning starting vicinity and in the scanning finishing vicinity are calculated on the basis of the X-ray irradiation column number n(t) calculated in step S103. Details of the process in step S105 will be described later.

(Step S106)

The system control device 124 calculates an exposure dose on the basis of the X-ray irradiation column number, the optimal tube current, and the collimator control quantity obtained through the processes in steps S103 to S105. Details of the process in step S106 will be described later.

(Step S107)

The system control device 124 preferably displays, on the display device 125, one or more of a temporal change in the X-ray irradiation region, a temporal change in the irradiation X-ray dose, and the exposure dose as a user interface.

Specifically, the optimal tube current I(t) calculated in step S104 or the exposure dose calculated in step S106 is displayed. Specifically, it is preferable to display one or more of a temporal change graph (FIG. 11(B)) of the optimal tube current I(t), a temporal change graph (FIG. 5 or the like) of an X-ray irradiation column number of an umbra, a temporal change graph (FIG. 15) of the number of columns corresponding to a penumbra half value width which will be described later, a temporal change graph (FIG. 16) of an exposure dose in the body axis direction, a temporal change graph of an exposure range, an average value of a tube current in the body axis direction, an integrated value of an exposure dose, a state transition diagram (FIG. 8 or the like) of an X-ray irradiation region 201, and the like.

A slicing position of the X-ray source 101 is uniquely defined according to time, and thus a transverse axis of each of the above-described graphs may express a slicing position of the X-ray source 101 instead of time. For better understanding of comparison between a slicing position and a value of each parameter, as illustrated in FIG. 11(A), a scanogram image and a graph may be displayed to overlap each other.

Figure 15:
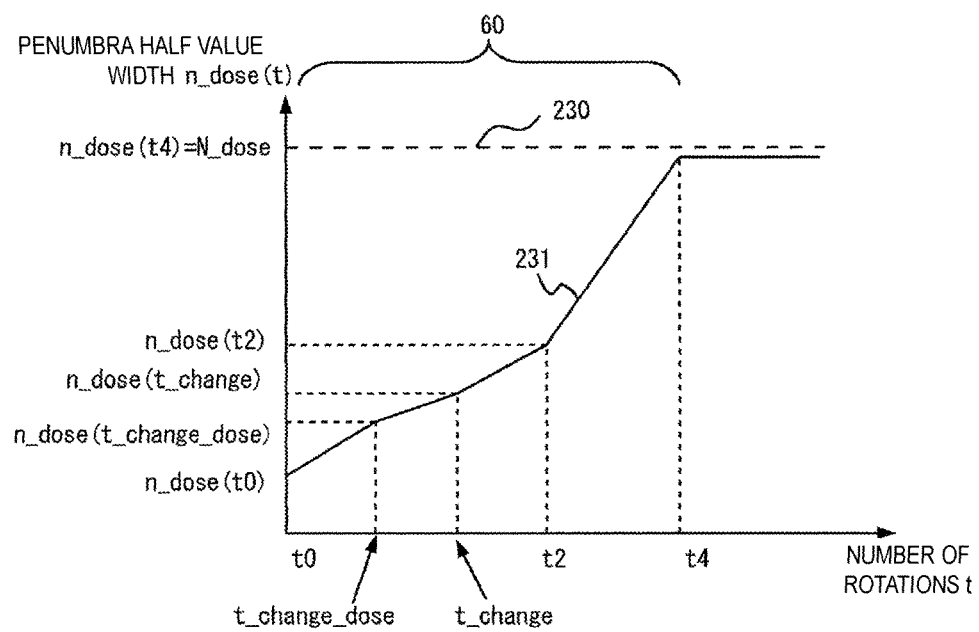
FIG. 15 is a graph illustrating a temporal change of the number of columns n_dose(t) corresponding to a penumbra half value width.
Figure 16:
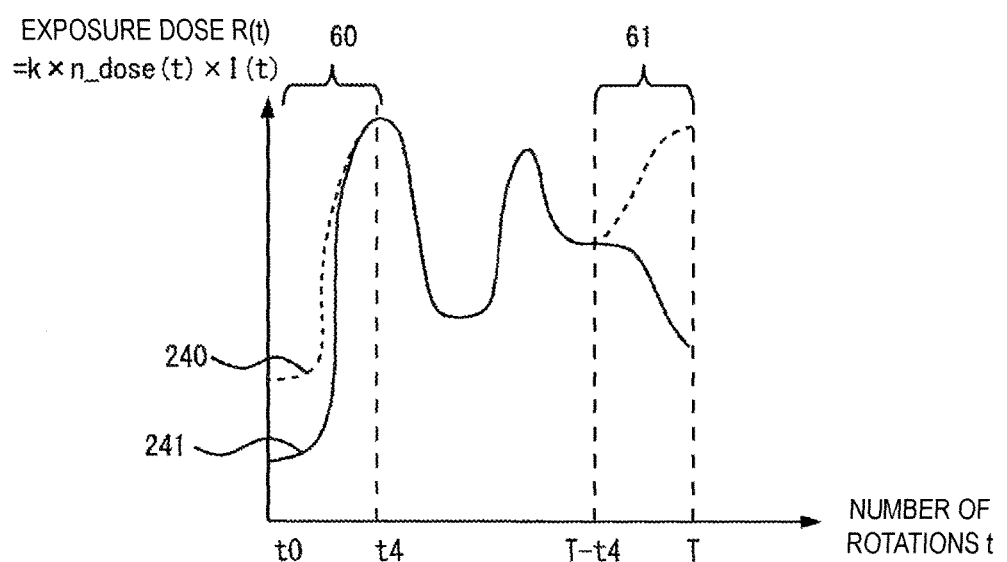
FIG. 16 is a diagram for explaining an exposure dose reduction effect in the first embodiment.

In order to visually check an effect of dose optimization of the present invention, as illustrated in FIG. 11(B), an optimal tube current (207) of the related art and an optimal tube current (208) of the present invention may be displayed so as to be compared with each other. In order to visually check an exposure dose reduction effect achieved by collimator control, as illustrated in FIG. 15, a penumbra half value width in a case where the collimator is stationary and a penumbra half value width in a case where the collimator is controlled may be displayed so as to be compared with each other, and, as illustrated in FIG. 16, exposure doses may be displayed so as to be compared with each other.

Figure 17:
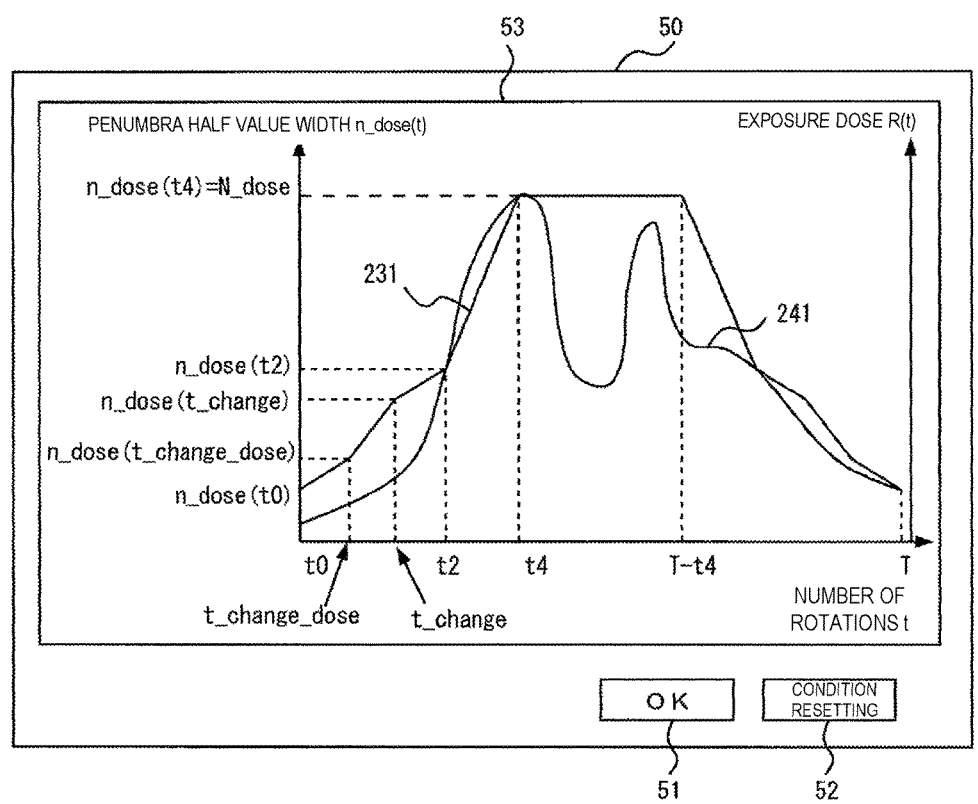
FIG. 17 illustrates an example of a user interface unit 50 (display screen).

The system control device 124 may display a display screen 50 as a user interface, as illustrated in FIG. 17, provided with a graph display region 53 in which various graphs regarding scanning are displayed, and an input part (an "OK" button 51 and a "condition resetting" button 52) for inputting an instruction for permitting or not permitting scanning with the content displayed in the graph display region 53.

(Step S108)

The operator refers to the display content such as the X-ray dose or the exposure dose displayed in step S107, and determines whether or not scanning is performed in the set examination conditions. In a case where it is determined that the conditions are appropriate for scanning, an "OK" instruction is input via the input device 121 (OK in step S108), and the flow proceeds to step S109. In a case where it is determined that the examination conditions are inappropriate for scanning, an "NG" instruction is input via the input device 121 (NG in step S108), the flow returns to step S102, and examination conditions are set again.

The inputting of the above-described "OK" and "NG" may be performed on the display screen of the user interface illustrated in FIG. 17, for example. If the "OK" button 51 is pressed, and an instruction for permitting scanning is input (OK in step S108), the system control device 124 starts scanning in the set examination conditions. On the other hand, if the "condition resetting" button 52 is pressed, and an instruction for not permitting scanning is input (NG in step S108), the flow proceeds to step S102 in order to reset examination conditions.

(Step S109)

The system control device 124 controls the collimators 10 according to the collimator positions L(t) calculated in step S105, and also performs X-ray irradiation based on the optimal tube current I(t) calculated in step S104, so as to perform helical scanning.

(Step S110)

The image reconstruction device 122 performs an image reconstruction process by using projection data obtained through the scanning in step S109 and the "reconstruction conditions during scanning". The system control device 124 stores a reconstructed image in the storage device 123 and also displays the reconstructed image on the display device 125.

(Step S111)

The system control device 124 performs post-reconstruction in response to an instruction from the operator. The post-reconstruction is a process of calling the projection data stored in the storage device 123 and reconstructing an image on the basis of post-reconstruction conditions. The post-reconstruction conditions may be different from the "reconstruction conditions during scanning" used for image reconstruction in step S110.

Next, a description will be made of the process of calculating the X-ray irradiation column number n(t) in step S103 in FIG. 3 with reference to FIGS. 4 to 7. The system control device 124 (X-ray irradiation region calculation unit 130) determines the X-ray irradiation column number n(t) which is necessary in image reconstruction after t rotations from a scanning starting time point by using examination conditions such as the beam width and the helical pitch.

Figure 4:
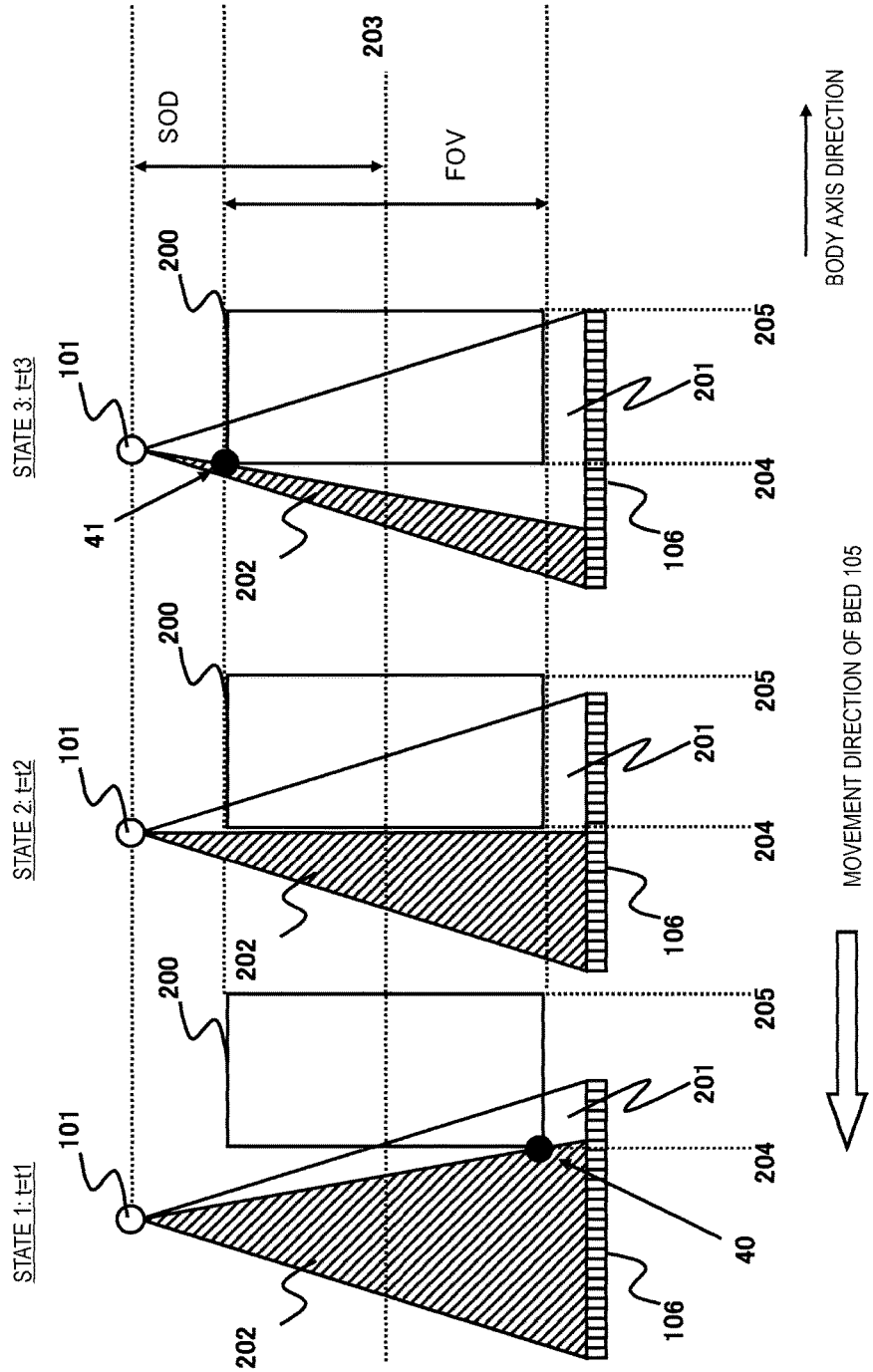
FIG. 4 is a state transition diagram of an X-ray irradiation region 201 in multi-slice CT.

FIG. 4 is a diagram illustrating an X-ray irradiation region 201 in which X-ray irradiation is necessary and an X-ray shield region 202 in which X-ray irradiation is unnecessary over time in order to create a leading image at a leading image position 204 of an image reconstruction region 200 set by the operator in step S102 in the scanning starting vicinity. As illustrated in FIG. 4, in a case where positions of the X-ray source 101 and the X-ray detector 106 in the body axis direction are fixed, and the bed 105 is moved to the left in FIG. 4 at bed velocity V, it is necessary to gradually increase an X-ray irradiation column number from the right column (referred to as a leading side column) of the X-ray detector 106 so as to widen the X-ray irradiation region 201.

An effective field of view of the image reconstruction region 200 is referred to as an FOV. For example, in order to create an image up to a side edge of the FOV, X-rays are required to be applied to a position 40 on the leading image position 204 farthest from the X-ray source 101 in a state 1 (t=t1) in FIG. 4. In a state 3 (t=t3) in FIG. 4, X-rays are required to be applied to a position 41 on the leading image position 204 closest to the X-ray source 101. The number of rotations when a focused position changes from the position 40 to the position 41 is set to t=t2.

The number of rotations when the X-ray irradiation column number n(t) matches the whole number of columns N of the X-ray detector 106, corresponding to the beam width, is set to t=t4. A scanning starting time point is also set to t=t0=0. Hereinafter, a case of t0<t2<t4 is assumed. The number of X-ray irradiation columns which are necessary at a scanning starting time point t=t0 is indicated by n(t0).

If a distance from the X-ray source 101 to the rotation center 203 is indicated by SOD (that is, source object distance), and a helical pitch is indicated by HP, the X-ray irradiation column number n(t) which is necessary in X-ray irradiation after t rotations from the scanning starting may be expressed by the following Equations (1) and (2) in two stages.

In the case of t0≤t≤t2:

$$n(t)=n(t0)+SOD/(SOD+FOV/2) \times HP \times t \quad (1)$$

In the case of t2<t≤t4:

$$n(t)=n(t2)+SOD/(SOD-FOV/2) \times HP \times (t-t2) \quad (2)$$

Here, t2 and n(t0) are determined depending on a reconstruction method, especially, an inverse projection phase width or a slice thickness.

For simplification, FIG. 4 illustrates a case (n(t2)=N/2) in which an exactly half columns of the whole number of columns N of the X-ray detector 106 corresponding to the beam width are irradiated with X-rays at t=t2, but it cannot be generally said that n(t2)=N/2. If an X-ray irradiation column number increased per unit number of rotations is indicated by Δn, Δn may be expressed as in the following Equations (3) and (4) by using Δn=n(t+1)−n(t), and the above Equations (1) and (2).

In the case of t0≤t≤t2:

$$\Delta n = SOD/(SOD+FOV/2) \times HP \quad (3)$$

In the case of t2<t≤t4:

$$\Delta n = SOD/(SOD-FOV/2) \times HP \quad (4)$$

Figure 5:
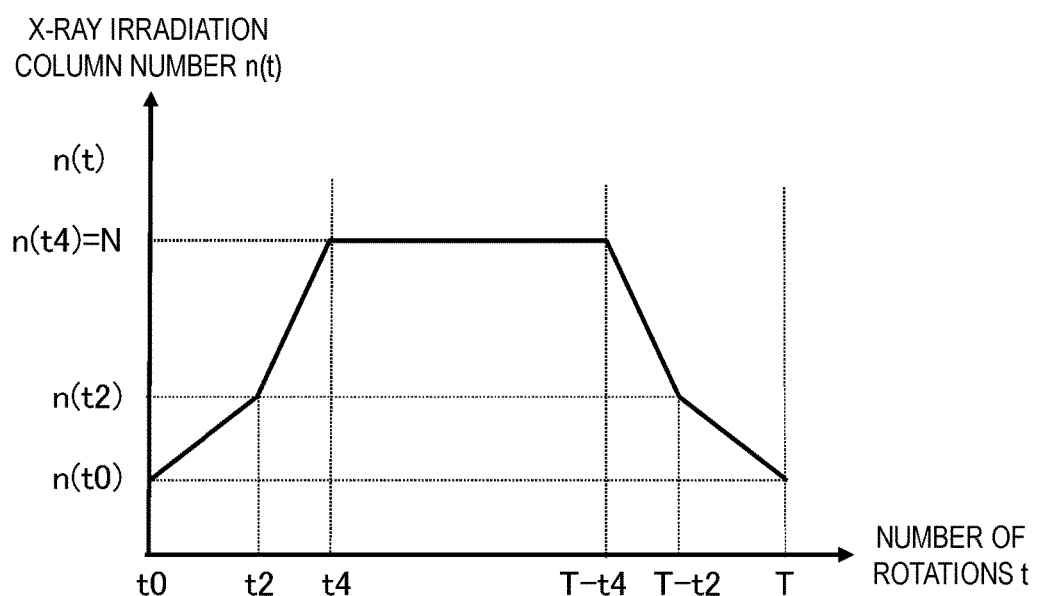
FIG. 5 is a graph illustrating a temporal change in the X-ray irradiation region (irradiation column number n(t)).

FIG. 5 illustrates an example of a temporal change graph (n(t) graph) of the X-ray irradiation column number n(t) from scanning starting t=t0=0 to scanning finishing t=T. The n(t) graph in FIG. 5 may be displayed in the display process in step S107. If the n(t) graph as in FIG. 5 is displayed, the operator can easily determine that the set examination conditions are appropriate in the determination of examination conditions in step S108.

Here, the FOV and the slice thickness are focused.

FIG. 6 is a diagram illustrating a difference in the X-ray irradiation column number n(t) due to the FOV. As illustrated in FIG. 6, the X-ray irradiation column number n(t) which is necessary after t rotations is larger (B) in a case where the FOV is large than (A) in a case where the FOV is small.

Figure 7:
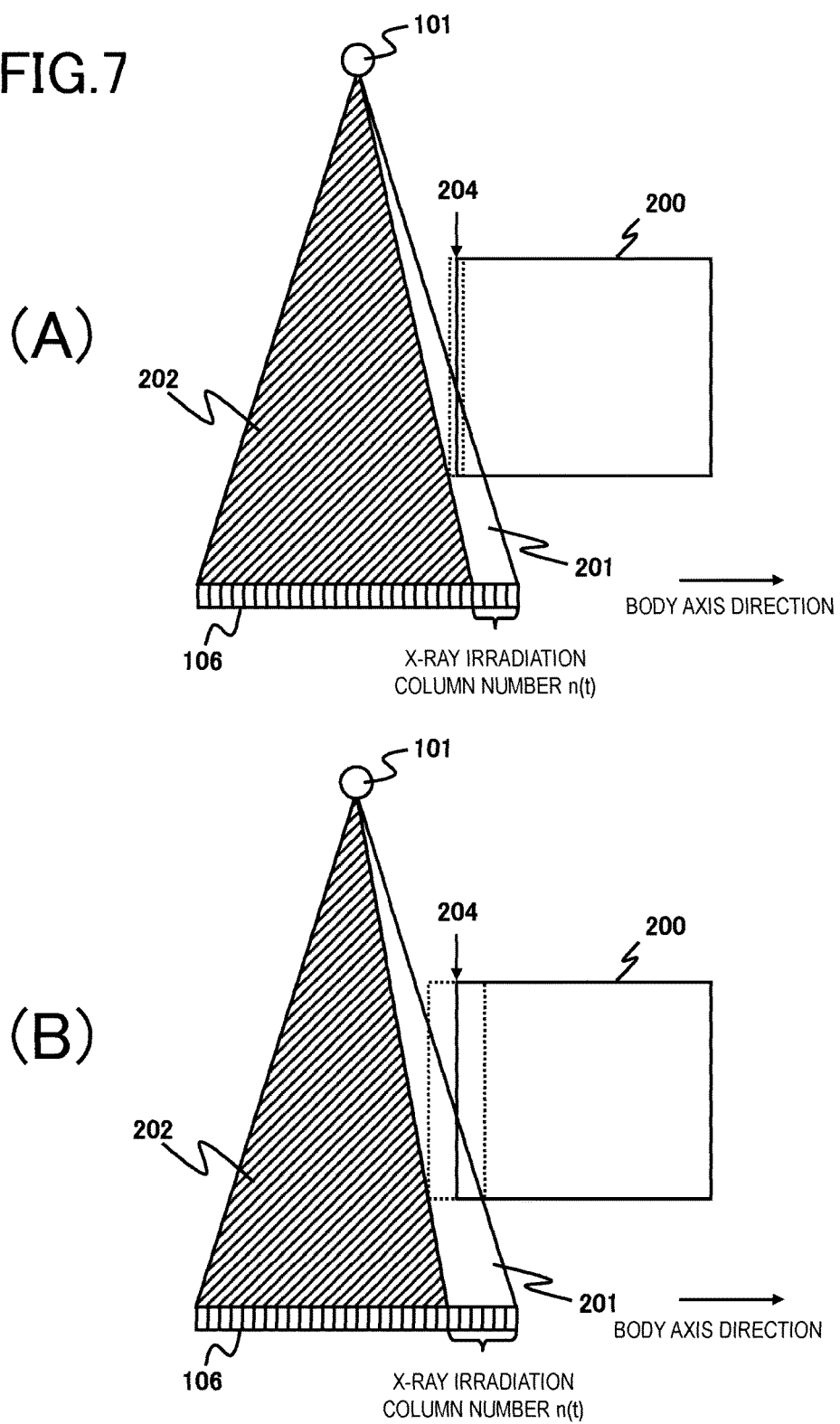
FIG. 7 is a diagram for explaining a difference in the X-ray irradiation region 201 due to a slice thickness.

FIG. 7 is a diagram illustrating a difference in the X-ray irradiation column number n(t) due to the slice thickness. As illustrated in FIG. 7, the X-ray irradiation column number n(t) which is necessary after t rotations is larger (B) in a case where the slice thickness is large than (A) in a case where the slice thickness is small, even if the leading image positions 204 in the image reconstruction region 200 are the same as each other. As mentioned above, n(t) depends on the FOV and the slice thickness, and is thus expressed as n(t, FOV, S).

Generally, there is a case where the operator may reconstructs an image in separate conditions after scanning finishing in step S109 (post-reconstruction in step S111) by changing examination conditions including the FOV or the slice thickness. The post-reconstruction is a function of reconstructing an image in reconstruction conditions which are determined as being necessary in diagnosis on the basis of projection data acquired through scanning, without performing scanning again. For example, there is a case where a lesion which is desired to be observed is enlarged so as to perform reconstruction, an image is reconstructed by using central coordinates of the image in order to observe a lesion separated from the rotation center, an image is reconstructed with a small slice thickness in order to reduce a partial volume effect, or an image is reconstructed with a large slice thickness in order to reduce image noise.

An FOV and a slice thickness which are set by the operator during scanning as "reconstruction conditions during scanning" are respectively referred to as a scanning FOV (FOV_scan) and a scanning slice thickness (S_scan), and an FOV and a slice thickness which are set during post-reconstruction as post-reconstruction conditions are respectively referred to as a reconstruction FOV (FOV_recon) and a reconstruction slice thickness (S_recon). It is assumed that scanning is performed with an X-ray irradiation column number n(t, FOV_scan, S_scan) which is the optimum for obtaining an image at the scanning FOV and the scanning slice thickness. In this case, the operator can acquire the image at the scanning FOV and the scanning slice thickness with the minimum exposure dose.

However, in a case where an image at FOV_recon>FOV_scan and S_recon>S_scan is to be reconstructed in the post-reconstruction, image reconstruction requires projection data of n(t, FOV_recon, S_recon) columns more than projection data of n(t, FOV_scan, S_scan) columns acquired during scanning. Since the projection data of n(t, FOV_recon, S_recon) columns is not acquired during scanning, projection data required to obtain an image at the reconstruction FOV and the reconstruction slice thickness is deficient, and thus an image in the post-reconstruction conditions cannot be obtained in the vicinity of a leading image or in the vicinity of a tailing image. If an image at FOV_recon>FOV_scan and S_recon>S_scan is to be obtained in the vicinity of a leading image or in the vicinity of a tailing image, the object is inevitably scanned again, and thus an exposure dose of the object increases.

Therefore, the X-ray irradiation column number n(t) is naturally determined in light of post-reconstruction conditions. For example, in the examination condition setting in step S102, the operator may set a reconstruction FOV and a reconstruction slice thickness which may possibly be set in post-reconstruction, separately from the scanning FOV and the scanning slice thickness. In this case, the system control device 124 uses a larger FOV of the scanning FOV and the reconstruction FOV, and the system control device 124 calculates the X-ray irradiation column number n(t) by using a larger slice thickness of the scanning slice thickness and the reconstruction slice thickness.

Alternatively, the system control device 124 may calculates an X-ray irradiation column number n(t, FOV_max, S_max) by using the maximum FOV (FOV_max) and the largest slice thickness (S_max). In this case, the operator can save time and effort to set a reconstruction FOV and a reconstruction slice thickness, and can create images in all reconstruction conditions during post-reconstruction.

In a case where the collimator unit 103 is provided with various types of X-ray compensation filters for adjusting an X-ray distribution in the channel direction, FOV_max may be changed according to selection of the X-ray compensation filter which is one of the examination conditions.

As described above, in a case where the X-ray irradiation column number n(t) is calculated by taking into consideration the reconstruction FOV and the reconstruction slice thickness, and the collimators 10 are controlled as described in step S105 which will be described later, an X-ray dose can be reduced in the scanning starting vicinity and in the scanning finishing vicinity, compared with scanning of the related art in which the X-ray irradiation column number n(t) is not changed, and post-reconstruction can be performed in any condition desired by the operator. Thus, it is possible to prevent a situation in which an image cannot be created in the vicinity of a leading image or in the vicinity of a tailing image.

In the above description, an FOV and a slice thickness have been described as representatives, but, if there is a parameter in which ranges of columns contributing to image reconstruction are different from each other in "reconstruction conditions during scanning" and post-reconstruction conditions, such as FOV central coordinates, a reconstruction function, and filter processing in a Z direction, needless to say, the parameter may be treated in the same manner as the FOV or the slice thickness.

In step S103, n(t) may be computed according to the examination conditions in step S102 as described above, and n(t) may be calculated in advance in each examination condition so as to be preserved in the system control device 124, and n(t) may be read from the system control device 124 according to the examination conditions in step S102. Particularly, if important values such as t0, t2, t4, n(t0), n(t2), and Δn are calculated in advance, and are preserved in the system control device 124, n(t) can be easily calculated with respect to any number of rotations t, and thus it is possible to reduce computation time.

Next, a description will be made of the process of calculating the optimal tube current I(t) in step S104 with reference to FIGS. 8 to 10. There is a technique (auto exposure control: AEC) of appropriately controlling a dose of X-rays applied to an object in order to maintain image quality desired by an operator. This is a technique of optimizing a dose and image quality having a tradeoff relationship with good balance, and image noise or a contrast-to-noise ratio (CNR) is used as an image quality index.

A position of the X-ray source 101 in the body axis direction after t rotations from a scanning starting time point is indicated by Z(t). In AEC of the related art, the optimal tube current I(t) in a case where the X-ray source 101 is located at Z(t) is calculated by using a slicing position Z(t), or scanogram projection data or a pixel value of a region centering on the slicing position Z(t). However, in a case where the X-ray irradiation region 201 used for image reconstruction dynamically changes, it cannot necessarily be said that an optimal tube current at the slicing position Z(t) is an optimal tube current for the X-ray irradiation region 201. Therefore, a slicing position for calculating an optimal tube current is selected from the X-ray irradiation region 201, and then an optimal tube current I(t) in the X-ray irradiation region 201 is calculated.

When the X-ray source 101 is located at Z(t), n(t) columns of the X-ray detector 106 are irradiated with X-rays. In this case, slicing positions of the respective detector columns irradiated with X-rays at the rotation center are sequentially indicated by Z(t)_i (where i=1, 2, 3, ..., and n(t)).

Figure 8:
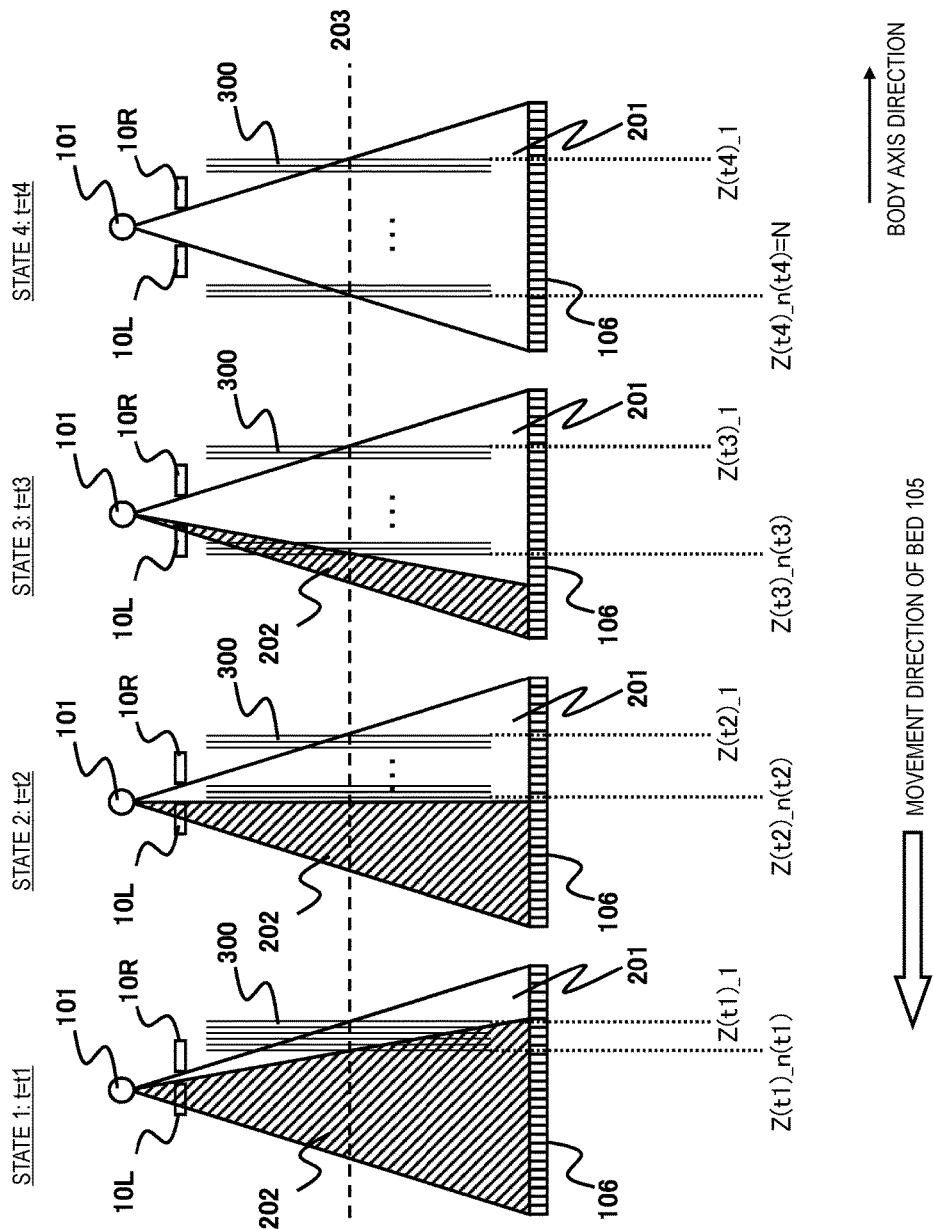
FIG. 8 is a state transition diagram of an analysis line 300 which is set to calculate an optimal tube current I(t)_i.

FIG. 8 illustrates the X-ray irradiation region 201, the X-ray shield region 202, and the slicing positions Z(t)_i (where i=1, 2, 3, ..., and n(t)) over time in the scanning starting vicinity. The Z(t)_1 side is assumed to be a leading side column, and the Z(t) n(t) side is assumed to be a tailing side column.

In the X-ray CT apparatus 1 of the first embodiment, analysis lines 300 are set in the slicing positions Z(t)_i (where i=1, 2, 3, ..., and n(t)) in order to calculate a tube current. As illustrated in FIG. 8, the analysis lines 300 are assumed to be perpendicular to the bed 105 (body axis). In the scanogram scanning process in step S101, scanogram data is assumed to be acquired along the analysis lines 300.

Figure 9:
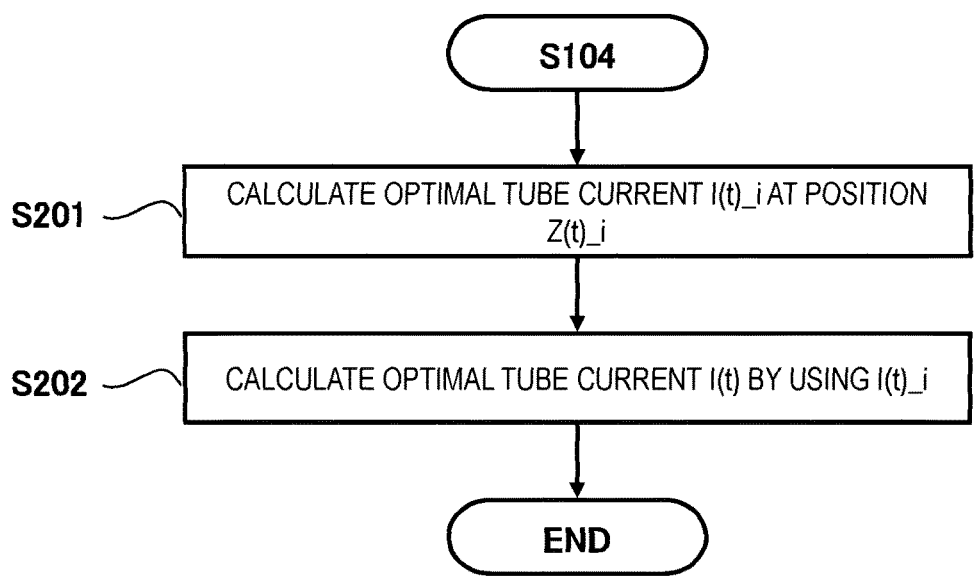
FIG. 9 is a flowchart illustrating procedures of a first optimal tube current calculation process.

FIG. 9 illustrates procedures of a first optimal tube current I(t) calculation process.

In the first optimal tube current I(t) calculation process, first, the system control device 124 calculates an optimal tube current I(t)_i at a slicing position Z(t)_i (step S201). For example, the system control device 124 creates a vertical sectional model of the object at the position Z(t)_i by using scanogram projection data on the analysis lines 300 at the slicing position Z(t)_i, so as to predict image noise, and calculates respective optimal tube currents I(t)_i (where i=1, 2, 3, ..., and n(t)) at the slicing positions Z(t)_i (where i=1, 2, 3, ..., and n(t)).

The system control device 124 calculates an optimal tube current I(t) in the X-ray irradiation region 201 by using I(t)_i calculated in step S201. For example, as shown in the following Equation (5), an average value of I(t)_i (where i=1, 2, 3, ..., and n(t)) of the respective columns is used as the optimal tube current I(t) (step S202).

$$I(t)=(I(t)\_1+I(t)\_2+\ldots+I(t)\_n(t))/n(t) \quad (5)$$

Instead of the average value, the maximum value or the minimum value of I(t)_i of the respective columns may be used as the optimal tube current I(t). In a case where the maximum value of I(t)_i of the respective columns is used as the optimal tube current I(t), an X-ray dose is sufficiently secured for the X-ray irradiation region 201, and thus it is possible to prevent a situation in which a dose is not sufficient with respect to image quality desired by the operator. On the other hand, in a case where the minimum value of I(t)_i of the respective columns is used as the optimal tube current I(t), a reduction in exposure of the X-ray irradiation region 201 can be prioritized while minimal image quality is maintained. In a case where the average value is used as the optimal tube current I(t) as described above, scanning is performed with an average X-ray dose, and thus it is possible to realize both reduction in exposure reduction and maintaining of image quality with good balance.

Any one of an average value, the maximum value, and the minimum value may be set to be selected by default, and may be selected by the operator. Recommended options may be displayed and selected in accordance with an examination purpose or an examination target.

Figure 10:
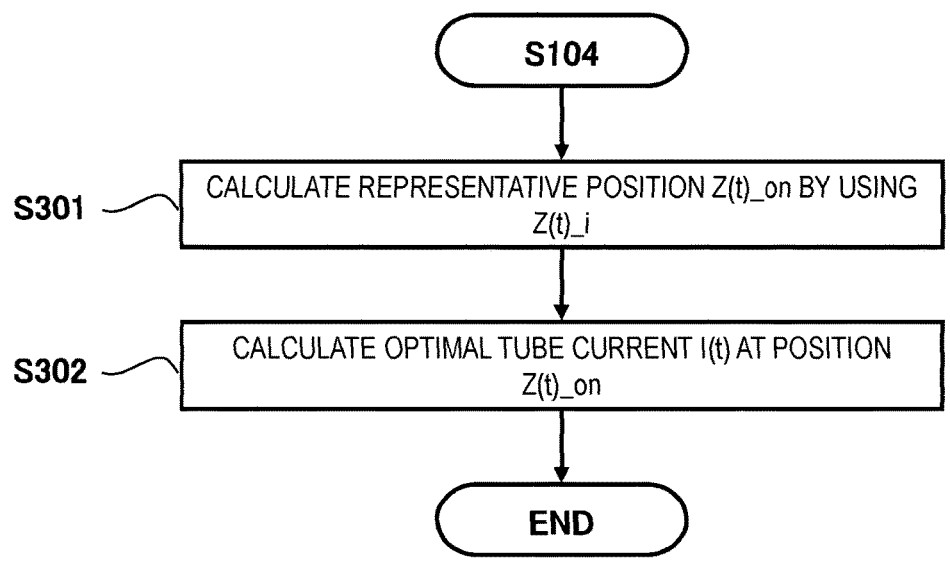
FIG. 10 is a flowchart illustrating procedures of a second optimal tube current calculation process.

FIG. 10 illustrates procedures of a second optimal tube current I(t) calculation process.

In the second optimal tube current I(t) calculation process, the system control device 124 calculates a representative slicing position Z(t)_on from slicing positions Z(t)_i (step S301). For example, as shown in the following Equation (6), an average value of Z(t)_i (where i=1, 2, 3, . . . , and n(t)) of the respective columns is used as the representative slicing position Z(t)_on.

$$Z(t)\_on=(Z(t)\_1+Z(t)\_2+ \ldots +Z(t)\_n(t))/n(t) \quad (6)$$

Instead of the average value, the maximum value or the minimum value of Z(t)_i of the respective columns, that is, a leading slicing position Z(t)_1 or a tailing slicing position Z(t)_n(t) in the X-ray irradiation region 201 may be used as the representative slicing position Z(t)_on. Alternatively, any slicing position Z(t)_i designated by the operator may be used as the representative slicing position Z(t)_on. Alternatively, a slicing position which is offset from the average value of Z(t)_i (where i=1, 2, 3, . . . , and n(t)) by a predetermined distance in a direction of the leading side column or a direction of the tailing side column may be used as the representative slicing position Z(t)_on.

Next, the system control device 124 calculates an optimal tube current I(t) at the representative slicing position Z(t)_on (step S302). For example, the system control device creates a vertical sectional model of the object at the position Z(t)_on by using scanogram projection data on the analysis lines 300 at the position Z(t)_on, so as to predict image noise, and calculates an optimal tube current I(t) at the slicing position Z(t)_on.

When compared with the first optimal tube current calculation process illustrated in FIG. 9, in the second optimal tube current calculation process illustrated in FIG. 10, a process of calculating the optimal tube current I(t) by using the slicing position Z(t)_i is performed once, and thus it is possible to reduce computation time.

As described above, the X-ray CT apparatus 1 of the present invention dynamically changes the X-ray irradiation region 201 for each view angle during scanning and also obtains an irradiation X-ray dose which is the optimum for each X-ray irradiation region 201. Consequently, for example, in a case where an X-ray irradiation region is deviated in the body axis direction relative to a slicing position of the X-ray source in the scanning starting vicinity or in the scanning finishing vicinity during helical scanning or the like in multi-slice CT, an appropriate X-ray dose for the X-ray irradiation region can be obtained. Particularly, the present invention is characterized in that positions of the analysis lines 300 used for calculation of an optimal tube current are changed during scanning according to the X-ray irradiation region 201. Consequently, for example, in a case where a beam width is large in a multi-column X-ray detector, the leading image position 204 or a tailing image position 205 of the image reconstruction region 200 is located at a part steep in the body axis direction, and an optimal tube current at positions of the analysis lines 300 is greatly different from an optimal tube current of the related art at an X-ray source position (slicing position Z(t)), a dose optimization effect achieved by the present invention is increased. As scanning with a larger beam width is performed by using a detector with more columns, a difference between a position of the analysis line 300 and the slicing position Z(t) easily increases, and thus a dose optimization effect achieved by the present invention is increased.

An effect achieved by the present invention will be described with reference to FIG. 11. FIG. 11 illustrates a case where the leading image position 204 of the image reconstruction region 200 is located at the shoulder of an object 206 in the scanning starting vicinity, and scanning is started from the neck to the shoulder in order to create an image of the shoulder.

FIG. 11(A) illustrates the X-ray source 101, the image reconstruction region 200, a positional relationship of the leading image position 204, the X-ray irradiation region 201, and the X-ray shield region 202 in the scanning starting vicinity. FIG. 11(B) illustrates a temporal change graph of the optimal tube current I(t) at the slicing position Z(t) from starting of scanning to finishing of the scanning. In the graph illustrated in FIG. 11(B), a transverse axis expresses the number of rotations t from a scanning starting time point, but a slicing position of the X-ray source 101 is uniquely defined according to time, and thus the transverse axis may express time or a slicing position of the X-ray source 101 instead of the number of rotations.

A dashed curve 207 in FIG. 11(B) indicates an optimal tube current in a case where AEC of the related art is used, and a solid curve 208 in FIG. 11(B) indicates an optimal tube current in a case where the optimal tube current calculation process (steps S103 and S104 in FIG. 3) of the present invention is used. However, the curve 207 and the curve 208 overlap each other except for "the scanning starting vicinity 60 and the scanning finishing vicinity 61".

In AEC of the related art, an optimal tube current is calculated by normally using the analysis line 300 at a slicing position of the X-ray source 101. In FIG. 11(A), a slicing position of the X-ray source 101 is a position completely deviated relative to the X-ray irradiation region 201, and thus there is deviation between the X-ray irradiation region 201 and a position where the optimal tube current is calculated. Since the neck and the shoulder have great differences in X-ray attenuation, if an optimal tube current calculated in the vicinity of the neck at the position of the X-ray source 101 is applied to the vicinity of the shoulder in the X-ray irradiation region 201, a dose is insufficient for the shoulder, and thus there is concern that quality of an image of the vicinity of the leading image position 204 may deteriorate. Therefore, if the optimal tube current calculation process of the present invention is used, a tube current which is also the optimum for the X-ray irradiation region 201 located at a position deviated relative to the X-ray source 101 in the body axis direction can be applied to the X-ray irradiation region 201. Thus, in the scanning starting vicinity 60 or the scanning finishing vicinity 61, there is no dose deficiency or dose excess, and quality of an image of the vicinity of the leading image position 204 or an image of the vicinity of the tailing image position 205 is appropriately maintained.

The tube current graph in FIG. 11(B) may be displayed in step S107 in FIG. 3. The tube current graph as in FIG. 11(B)

is displayed, and thus the operator can easily determine whether or not scanning conditions are appropriate in step S108.

Next, a description will be made of the collimator position calculation process in step S105 in FIG. 3 with reference to FIGS. 8, 12 and 13. The collimator position calculation process in step S105 is a process of calculating a collimator position for reliably applying X-rays to the X-ray irradiation column number n(t) calculated in the X-ray irradiation column number calculation process in step S103 of FIG. 3.

For example, the collimators 10 of the collimator unit 103 have a plate-shaped left collimator 10L and right collimator 10R, and has a structure in which the collimator control device 111 can separately control the left collimator 10L and the right collimator 10R in the body axis direction during scanning. The collimators 10 are formed of a shield plate having a high X-ray absorption coefficient such as lead. A process described below is not limited to a case where the left collimator 10L and the right collimator 10R are separately controlled as described above, and is applicable to a mechanism having a structure for performing integral control in order to implement the simpler mechanism. The left collimator 10L and the right collimator 10R may be moved in the body axis direction, and may be moved in the vertical direction or the channel direction. A shape of the collimators 10 is not limited to a plate shape, and may be an arc shape or a spherical shape. The number of collimators 10 is also not limited to two.

FIG. 8 illustrates operations of the collimators 10 in the scanning starting vicinity over time. In a case where the bed 105 is moved to the left in FIG. 8, the left collimator 10L is required to be opened to the left so that the X-ray irradiation region 201 is reliably irradiated with X-rays.

First, a description will be made of a spreading width of a focal point 20 of the X-ray source in the body axis direction, radiated from the X-ray source 101. Generally, the focal point 20 of the X-ray source 101 has a spreading width in the channel direction and the body axis direction, and a spreading width in the body axis direction is indicated by L_Focal. Since the focal point 20 is spread in the body axis direction, X-rays incident to the X-ray detector 106 have an umbra and a penumbra. The umbra of the X-rays is preferably reliably incident to the X-ray irradiation column number n(t) required in reconstruction. This is because the penumbra of the X-rays has an X-ray dose smaller than that of the umbra of the X-rays, so as to cause deficiency of an X-ray dose for creating an image, and this leads to image quality deterioration such as a reduction in image noise. In a case where a focal point size can be selected as one of examination conditions, a value of L_Focal may be changed according to selection of the focal point size.

FIG. 12 illustrates the focal point 20 of the X-ray source, a positional relationship of the collimators 10, a region 210 with which the umbra comes into contact, and a region 211 with which the penumbra comes into contact, for irradiating the X-ray irradiation column number n(t) with the umbra of the X-rays.

Hereinafter, a description will be made of a method of calculating positions of the collimators 10 for irradiating the X-ray irradiation column number n(t) with the umbra of the X-rays after t rotations from starting of X-ray irradiation in the scanning starting vicinity. Particularly, herein, a right side surface 10L-PlaneR of the left collimator 10L illustrated in FIG. 12 is focused, and a distance between a central axis 212 of the focal point 20 and 10L-PlaneR is indicated by L(t).

First, a description will be made of influence of a thickness of each of the collimators 10 in the vertical direction on an X-ray irradiation range (umbra). For example, in the arrangement illustrated in FIG. 12(A), the irradiation range 210 of the umbra of the X-rays is determined at an upper end position of the right side surface 10L-PlaneR of the left collimator 10L. In the arrangement illustrated in FIG. 12(B), the irradiation range 210 of the umbra of the X-rays is determined at a lower end position of the right side surface 10L-PlaneR of the left collimator 10L. If the number of rotations when changing between the upper end and the lower end occurs is indicated by t=t_change, and a body axis direction length of a single element of the X-ray detector 106 at the rotation center is indicated by D, t_change is the number of rotations satisfying the following Equation (7).

$$n(t\_change) \lambda D = N \times D/2 + L\_Focal/2 \tag{7}$$

If a vertical distance from the focal point 20 to the upper surface of each of the collimators 10 is indicated by Lc_upper, and a vertical distance from the focal point 20 to the lower surface of each of the collimators 10 is indicated by Lc_lower, the system control device 124 may control a position of the left collimator 10L so as to satisfy the following Equations (8) and (9).

In the case of t≤t_change:

$$L(t)(N \times D/2 + L\_Focal/2 - n(t) \times Lc\_upper/SOD - L\_Focal/2 \tag{8}$$

In the case of t_change<t:

$$L(t)(N \times D/2 + L\_Focal/2 - n(t) \times Lc\_lower/SOD - L\_Focal/2 \tag{9}$$

If a movement distance of L(t) per unit number of rotations is indicated by ΔL, ΔL may be expressed by the following Equations (10) and (11) by using ΔL=L(t+1)−L(t), and Δn=n(t+1)−n(t).

In the case of t≤t_change:

$$\Delta L = -\Delta n \times D \times Lc\_upper/SOD \tag{10}$$

In the case of t_change<t:

$$\Delta L = -\Delta n \times D \times Lc\_lower/SOD \tag{11}$$

A temporal relationship among t0, t2, t4, and the number of rotations t_change shown in Equation (7) depends on a length of L_Focal, an inverse projection phase width, or the like, but, in a case of t0<t_change<t2, Δn in Equations (3) and (4) is assigned to Equations (10) and (11), and thus collimator velocity Vc(t) can be obtained.

In the case of t0≤t≤t2:

$$Vc(t) = V \times Lc\_upper/(SOD + FOV/2) \tag{12}$$

In the case of t_change<t≤t2:

$$Vc(t) = V \times Lc\_lower/(SOD + FOV/2) \tag{13}$$

In the case of t2<t≤t4:

$$Vc(t) = V \times Lc\_lower/(SOD - FOV/2) \tag{14}$$

Here, in the above Equations (12) to (14), bed velocity V=HP×D is used.

If the collimator 10L is controlled so as to satisfy the position L(t) shown in Equations (8) and (9), the umbra of the X-rays can be reliably into the X-ray irradiation column number n(t).

If the collimators 10 are to be controlled assuming that the focal point 20 has a point shape without accurately taking into consideration a spreading width of the focal point 20, the umbra 210 does not comes into contact with the column vicinity at the corner of the X-ray irradiation region 201, and thus there is concern that data required in image reconstruction may be deficient. It is important to control the collimators 10 by taking into consideration a spreading width of the focal point 20.

If the collimators 10 are controlled without accurately taking into consideration the upper and lower end points of the collimators 10, necessary X-rays are partially transmitted through the collimator 10L, and thus there is concern that data required in image reconstruction may be deficient. Particularly, in a case where a cheap alloy of iron or copper is used as a material of the collimators 10, it is necessary to increase a thickness of each of the collimators 10 in order to increase a shield effect for the X-ray shield region 202, and thus it is important to control the collimators 10 by taking into consideration a thickness of each of the collimators 10.

As described above, the collimator position L(t) is calculated by accurately taking into consideration a spreading width of the focal point in the body axis direction and a vertical thickness of each of the collimators 10, and thus the X-ray irradiation region 201 can be reliably irradiated with the umbra of X-rays.

In a case where the plate-shaped collimators 10 are used in the channel direction, and a detector surface of the X-ray detector 106 has a curved shape in a state of being depressed when viewed from the focal point 20, an X-ray distribution is preferably taken into consideration.

Figure 13:
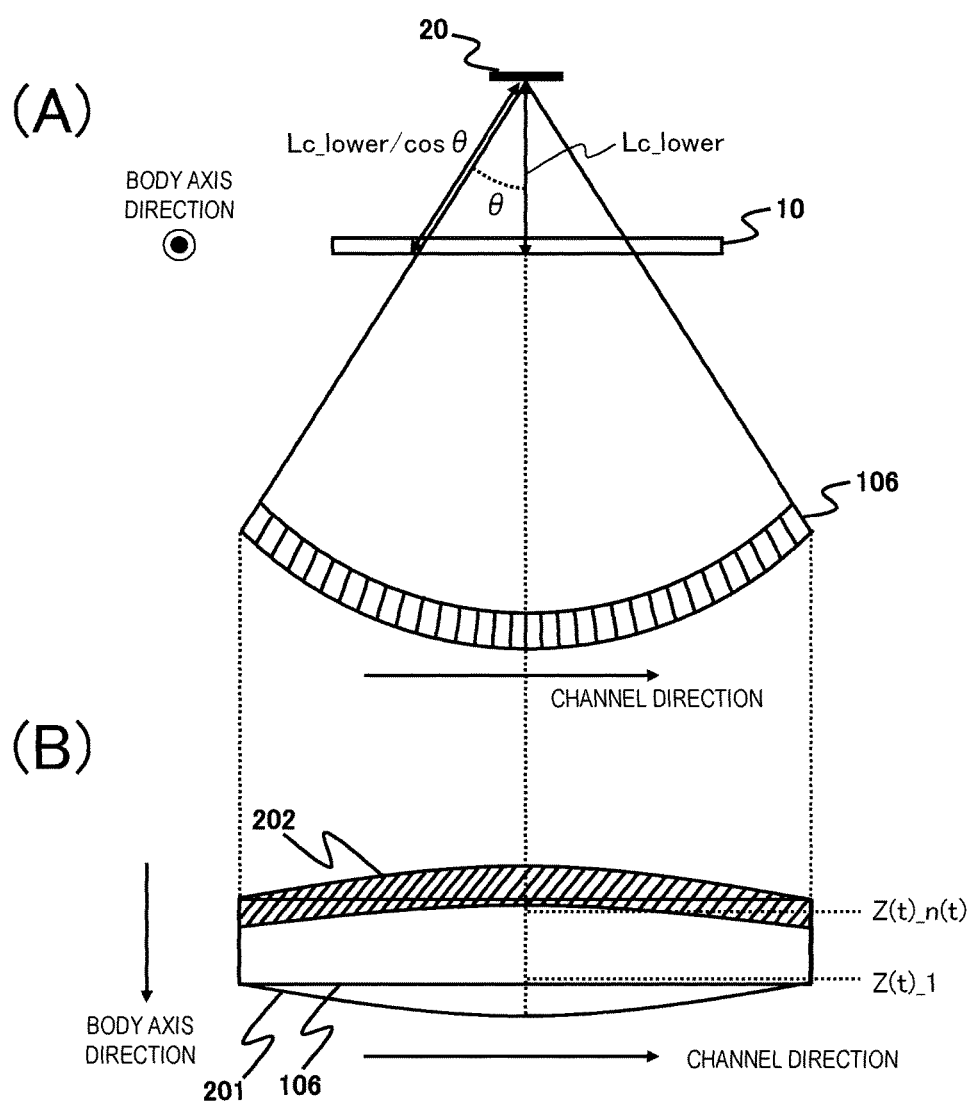
FIG. 13 is a diagram for explaining an example of calculating a collimator position corresponding to a swollen part of an X-ray distribution.

FIG. 13 is a diagram for explaining an X-ray distribution. FIG. 13(A) is a diagram in which the rotation disk 102 is viewed from the bed 105. FIG. 13(B) is a diagram in which the X-ray detector 106 is viewed from the focal point 20.

In a case where the focal point 20, the plate-shaped collimators 10, and X-ray detector 106 having a curved shape in a state of being depressed are provided in arrangement as in FIG. 13(A), a distribution of X-rays incident to the detector surface of the X-ray detector 106 is as in FIG. 13(B). As illustrated in FIG. 13(B), it is known that the X-ray distribution has a shape in which a central part is swollen more than both ends in the channel direction when viewed from the focal point 20.

In the above Equations (8) to (14), a collimator position is calculated so that the channel direction central part is irradiated with the umbra of X-rays by using the vertical distance Lc_lower from the focal point 20 to the collimator lower surface. In this case, the central part in the channel direction is irradiated with the umbra up to Z(t)_n(t) so that a necessary column number n(t) is satisfied as illustrated in FIG. 13(B), but channel direction both ends in which a distance from the focal point 20 to the collimator lower surface is long is not irradiated with the umbra up to Z(t)_n(t), and thus data required in image reconstruction is deficient.

Therefore, in a case where the X-ray distribution has a shape in which a central part is swollen more than both ends in the channel direction when viewed from the focal point 20, the system control device 124 may perform computation by replacing Lc_lower in the above Equations (8) to (14) with Lc_lower/cos θ. Here, θ is a half of the maximum open angle of the detector in the channel direction.

As mentioned above, by taking into consideration a swollen part of the X-ray distribution, even in a case where the plate-shaped collimators 10 and the X-ray detector 106 which is curved in a state of being depressed are used, the umbra of X-rays can be made to be incident to all detector elements in the channel direction so that the X-ray irradiation column number n(t) is satisfied.

In a case where an X-ray distribution does not have a swollen shape when viewed from the X-ray source 101, such as a case where the plate-shaped collimators 10 and the planar X-ray detector 106 are used, or a case where the collimators 10 having a curved shape similar to a depressed state of the X-ray detector 106 is used, the above-described consideration is not necessary.

In step S105, L(t) may be computed according to the X-ray irradiation column number n(t) and parameters (a focal point size L_Focal, a thickness of each of the collimators 10, a channel direction open angle θ, a length D of a single element of the X-ray detector in the body axis direction, and the like) of the system in each examination condition as described above, and L(t) may be calculated in advance in each examination condition so as to be preserved in the system control device 124, and L(t) may be read from the system control device 124 according to the examination conditions in step S102. Particularly, if important values such as t0, t_change, t2, t4, L(t0), L(t_change), L(t2), and ΔL are calculated in advance, and are preserved in the system control device 124, L(t) can be easily calculated with respect to any number of rotations t, and thus it is possible to reduce computation time.

Figure 14:
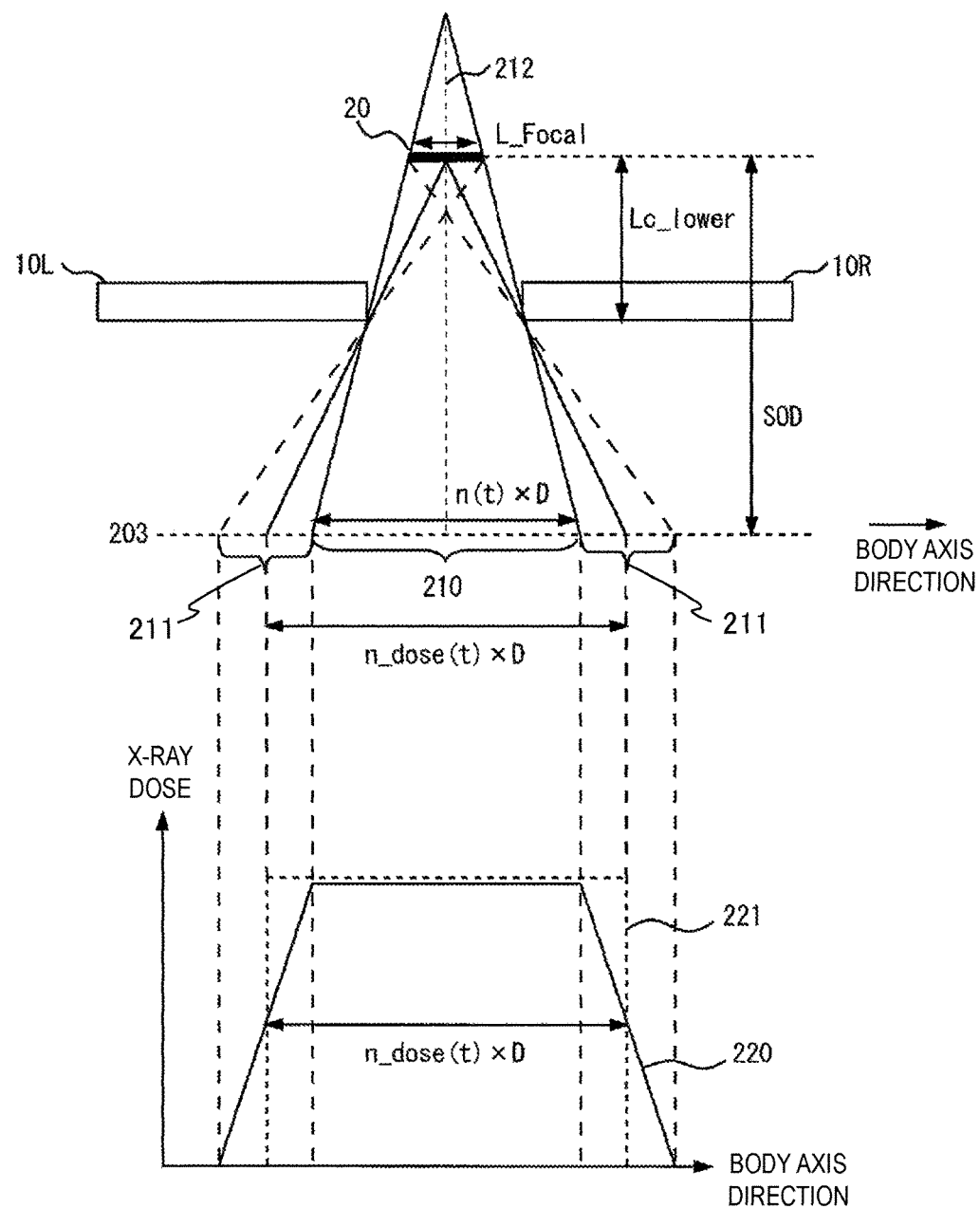
FIG. 14 is a diagram for explaining the number of columns n_dose(t) corresponding to a penumbra half value width.

Next, a description will be made of the exposure dose calculation process in step S106 in FIG. 3 with reference to FIGS. 14 to 16. In step S106, not only an exposure dose R(t) but also an integrated value R of exposure doses over the entire scanning range, or an exposure range W(t) may be calculated as information regarding exposure.

In a dose of X-rays applied to an object, an X-ray distribution not only related to the umbra but also related to the penumbra is required to be taken into consideration. FIG. 14 illustrates an X-ray dose distribution in the body axis direction after t rotations. As in a solid line 220 in FIG. 14, it is assumed that an X-ray dose is distributed in a trapezoidal shape in the body axis direction. An X-ray dose after t rotations is proportional to an area (an integrated value in the body axis direction) of the trapezoidal distribution 220. If the number of columns (hereinafter, referred to as a penumbra half value width) in which an X-ray dose related to the penumbra is a half value of an X-ray dose related to the umbra is indicated by n_dose(t), the area of the trapezoidal distribution 220 is the same as an area of a rectangular distribution 221 using n_dose(t). n_dose(t) is the same as an X-ray irradiation column number after t rotations, computed by assuming that the spreading width L_Focal of the focal point is 0.

As described above, if the vertical thickness of each of the collimators 10 is taken into consideration, there is a case where a penumbra half value width of X-rays is determined at the upper end of the right side surface 10L-PlaneR of the left collimator 10L and a case where a penumbra half value width of X-rays is determined at the lower end of the right side surface 10L-PlaneR of the left collimator 10L. If the number of rotations when changing between the upper end and the lower end occurs is indicated by t=t_change_dose, t_change_dose is the number of rotations satisfying the following Equation (15).

$$L(t\_change\_dose)=0 \qquad (15)$$

If a penumbra half value width when the umbra is applied to the whole number of columns N is indicated by N_dose, N_dose satisfies the following Equation (16).

$$N\_dose \times D=((N \times D-L\_Focal) \times Lc\_lower/SOD-L\_Focal) \times SOD/Lc\_lower \qquad (16)$$

Generally, n_dose(t) is expressed by Equations (17) and (18).

In the case of t≤t_change_dose:

$$n\_dose(t)=(N\_dose \times D/2-L(t) \times SOD/Lc\_upper)/D \qquad (17)$$

In the case of t_change_dose<t:

$$n\_dose(t)=(N\_dose \times D/2-L(t) \times SOD/Lc\_lower)/D \quad (18)$$

If the number of columns corresponding to a penumbra half value width increasing per unit number of rotations is indicated by Δn_dose, Δn_dose may be expressed by the following Equations (19) and (20) by using Δn_dose=n_dose (t+1)−n_dose (t) and ΔL=L(t+1)−L(t).

In the case of t≤t_change_dose:

$$\Delta n\_dose = \Delta L \times SOD/Lc\_upper/D \quad (19)$$

In the case of t_change_dose<t:

$$\Delta n\_dose = \Delta L \times SOD/Lc\_lower/D \quad (20)$$

Here, in a case of L_Focal≥0, t_change_dose≥t_change is satisfied.

A temporal relationship among t0 and the number of rotations t_change_dose shown in Equation (15) depends on an inverse projection phase width or the like, but, in a case of t0<t_change_dose≤t_change<t2<t4, ΔL in Equations (10) and (11), and Δn in Equations (3) and (4) are assigned to Equations (19) and (20), and results thereof may be expressed by the following Equations (21) to (24).

In the case of t0≤t≤t_change_dose:

$$\Delta n\_dose = SOD/(SOD+FOV/2) \times HP \quad (21)$$

In the case of t_change_dose<t≤t_change:

$$\Delta n\_dose = SOD/(SOD+FOV/2) \times HP \times Lc\_upper/Lc\_lower \quad (22)$$

In the case of t_change<t≤t2:

$$\Delta n\_dose = SOD/(SOD+FOV/2) \times HP \quad (23)$$

In the case of t2<t≤t4:

$$\Delta n\_dose = SOD/(SOD-FOV/2) \times HP \quad (24)$$

FIG. 15 illustrates an example of a temporal change graph of n_dose(t) in the scanning starting vicinity 60. A dashed line 230 in FIG. 15 indicates a penumbra half value width in scanning of the related art in which the collimators 10 are stationary during scanning, and n_dose(t)=N_dose regardless of t. On the other hand, a solid line 231 in FIG. 15 indicates a penumbra half value width in the present invention in which the collimators 10 are dynamically controlled during scanning.

In step S106, n_dose(t) may be computed according to a position L(t) of each of the collimators 10 for each examination condition as described above, and n_dose(t) may be calculated in advance in each examination condition so as to be preserved in the system control device 124, and n_dose(t) may be read from the system control device 124 according to the examination conditions in step S102. Particularly, if important values such as t0, t_change_dose, t_change, t2, t4, n_dose(t0), n_dose(t_change_dose), n_dose(t_change), n_dose(t2), and Δn_dose are calculated in advance, and are preserved in the system control device 124, n_dose(t) can be easily calculated with respect to any number of rotations t, and thus it is possible to reduce computation time.

An exposure dose after t rotations is proportional to a product of the penumbra half value width n_dose(t) and the optimal tube current I(t). If a proportion coefficient is k, an exposure dose R(t) after t rotations may be expressed by the following Equation (25).

$$R(t)=k \times n\_dose(t) \times I(t) \quad (25)$$

FIG. 16 illustrates an example of a temporal change graph of the exposure dose R(t).

A dashed line 240 in FIG. 16 indicates an exposure dose R_past(t) during scanning of the related art, and indicates a result obtained by performing computation according to the following Equation (26) by using the optimal tube current I_past(t) of the related art indicated by the dashed curve 207 in FIG. 11(B).

$$R\_past(t)=k \times N\_dose \times I\_past(t) \quad (26)$$

On the other hand, a solid line 241 in FIG. 16 indicates a result obtained by performing computation according to the above Equation (25) by using the optimal tube current I(t) which is calculated through the optimal tube current calculation process (step S104 in FIG. 3) of the present invention. However, the curve 240 and the curve 241 overlap each other except for "the scanning starting vicinity 60 and the scanning finishing vicinity 61". Since n_dose(t)N_dose is satisfied in the scanning starting vicinity 60 and the scanning finishing vicinity 61, the exposure can be reduced, and image quality is also appropriately maintained by applying the optimal tube current I(t) to the X-ray irradiation region.

An integrated value R of the exposure dose over the entire scanning range may be expressed by the following Equation (27) as an integrated value of R(t) from the scanning starting time point t=t0 to the scanning finishing time point t=T.

$$R=k \times \smallint (n\_dose(t) \times I(t))dt \quad (27)$$

The graph of the penumbra half value width n_dose(t) illustrated in FIG. 15, the graph of the exposure dose R(t) illustrated in FIG. 16, the integrated value R of the exposure dose may be displayed in the display process in step S107 of FIG. 3. This is displayed, and thus the operator can easily determine whether or not scanning conditions are appropriate in the scanning condition checking process in step S108 of FIG. 3. As illustrated in FIG. 17, the graph of the penumbra half value width n_dose(t) illustrated in FIG. 15 and the graph of the exposure dose R(t) illustrated in FIG. 16 may be displayed at the same time. The number of rotations on the transverse axis may be a slicing position.

A length of a full width of the penumbra at the rotation center, that is, a range W(t) in which the object is exposed to X-rays in the body axis direction may be calculated according to the following Equation (28).

$$W(t)=(n(t)+2 \times (n\_dose(t)-N(t))) \times D \quad (28)$$

In step S107 in FIG. 3, a temporal change in the exposure range W(t) or a slicing position change may be displayed. The scanogram image obtained through step S101 and the exposure range W(t) may be displayed at the same time. In a case where examination conditions are desired to be set to avoid exposure of a part highly sensitive to radiation, such as the lens, displaying the exposure range W(t) is useful to determine whether or not examination conditions in step S108 are appropriate.

As described above, in the X-ray CT apparatus 1 (multi-slice CT) of the first embodiment, the system control device 124 performs helical scanning. The system control device 124 calculates an X-ray irradiation region satisfying examination elements for each view angle, dynamically changes and sets a position of the analysis line 300 for calculating an optimal tube current amount for each view angle with respect to the calculated X-ray irradiation region, and appropriately controls a dose of applied X-rays at each view angle on the basis of an analysis result in the analysis line 300. Consequently, particularly, ineffective exposure which does not contribute to image reconstruction can be reduced in the scanning starting vicinity 60 and the scanning finishing vicinity 61, and thus quality of an image in the leading image vicinity and the tailing image vicinity can be appropriately maintained.

Since the collimators 10 are dynamically controlled so that the calculated X-ray irradiation region is reliably irradiated with X-rays, it is possible to appropriately control a dose of the X-rays applied to the calculated X-ray irradiation region.

Since the X-ray irradiation region is calculated by taking into consideration post-reconstruction conditions, an X-ray dose is not deficient, and quality of an image can be appropriately maintained, for example, even in a case where an FOV is larger or a slice thickness is larger during post-reconstruction than reconstruction conditions during scanning.

In the above description, the description has been made focusing on the case where the bed 105 is moved to the left in FIGS. 4 and 8 in the scanning starting vicinity 60, and this may also be applied to a case of the scanning finishing vicinity 61 or a case where a movement direction of the bed 105 is reversed. Particularly, the case of the scanning finishing vicinity 61 will be described later in a third embodiment.

In the above description, the X-ray irradiation column number n(t), the optimal tube current I(t), or the position L(t) of each of the collimators 10 is expressed as a function of the number of rotations t, but may be expressed as a function of a rotation angle (view) or a function of a position of the bed 105 in the body axis direction.

Second Embodiment

Figure 18:
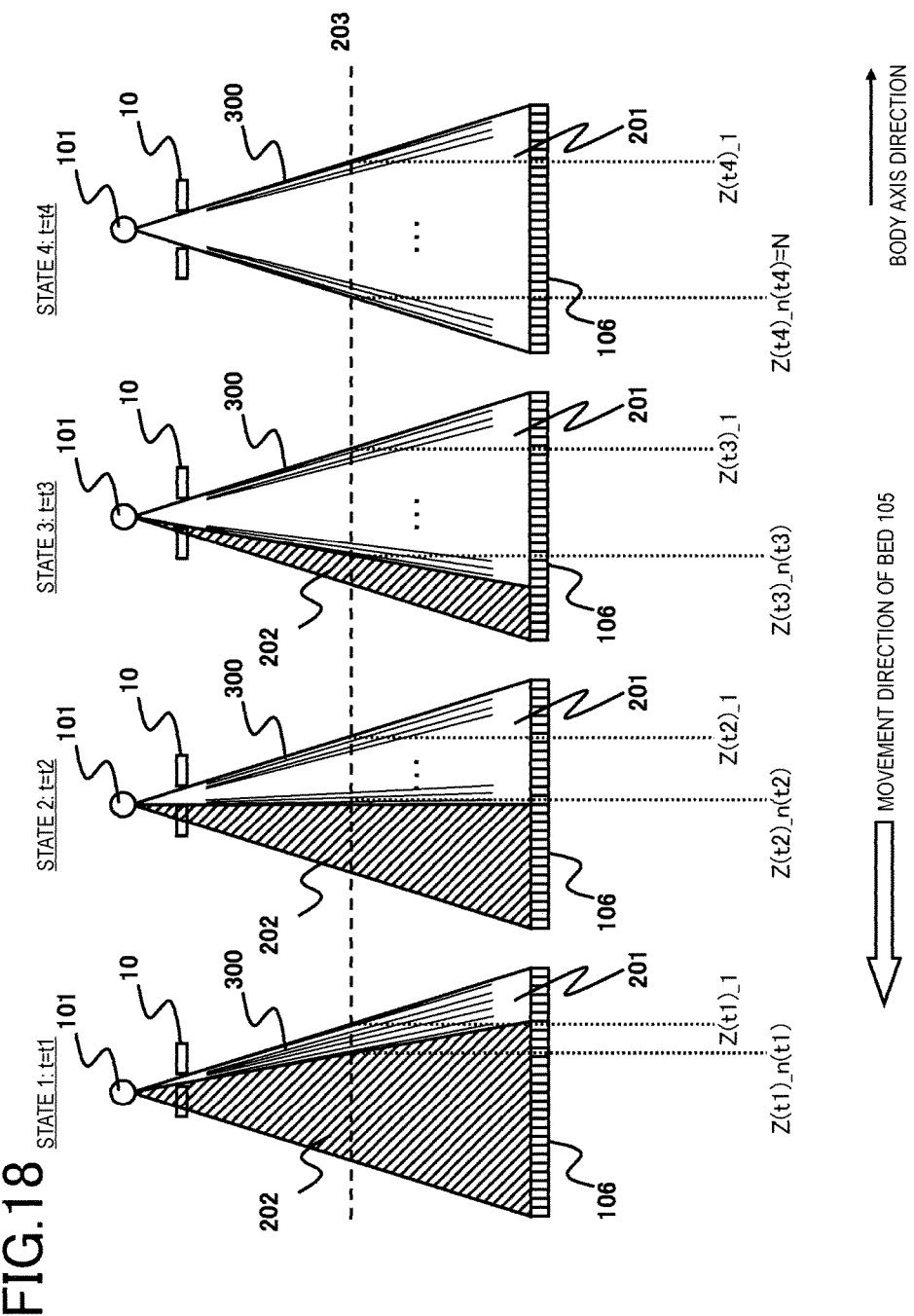
FIG. 18 illustrates a setting example of an analysis line 320 in a second embodiment.

Next, with reference to FIG. 18, a second embodiment of the present invention will be described.

A difference from the first embodiment is a process of calculating the optimal tube current I(t) (step S104 in FIG. 3). Hereinafter, only different parts will be described, and description of the same parts will be omitted.

When a sectional model is created in order to calculate the optimal tube current I(t), in the first embodiment, a section (the analysis line 300 in FIG. 8) perpendicular to the body axis is used. This is a simple and appropriate method since scanogram data indicates attenuation of each slicing position on a vertical section. However, an error corresponding to a cone angle occurs between the vertical section and a path with the cone angle along which X-rays are actually transmitted. Particularly, in a case where a beam width is large, or an object having a great change in the body axis direction is scanned, a difference between attenuation of the vertical section and attenuation of X-rays increases, and thus there is a probability that an X-ray dose may be deficient or excessive. Therefore, in the second embodiment, the optimal tube current I(t) is calculated by taking into consideration a cone angle of X-rays.

Since channels of the X-ray detector 106 are disposed in the vertical direction in LAT scanogram, regions corresponding to the number of detector channels are disposed in the vertical direction, and projection data is sampled at intervals of the detector channels. The system control device 124 (X-ray dose calculation unit 131) of the second embodiment sets an analysis line 320 with an angle with which X-rays are incident to the detector from the focal point, at any slicing position Z(t)_i. The system control device 124 (X-ray dose calculation unit 131) collects data regarding associated slicing positions and detector channels on the analysis line 320 so as to create projection data at the slicing position Z(t)_i.

In the first embodiment, projection data at the slicing position Z(t)_i is scanogram projection data at the slicing position Z(t)_i, but, the second embodiment is characterized in that scanogram projection data at slicing positions other than the slicing position Z(t)_i are partially used, and projection data at the slicing position Z(t)_i is created. Consequently, a sectional model on the analysis line 320 with an angle with respect to the body axis direction can be created, and thus it is possible to calculate the optimal tube current I(t) in which incidence directions of X-rays are taken into consideration by using the sectional model.

The optimal tube current calculation method of the second embodiment is useful in a case where, particularly, the X-ray irradiation region 201 includes a column with a large cone angle, and becomes more useful as a beam width becomes larger in a multi-column X-ray detector in which a cone angle increases.

Third Embodiment

Next, a third embodiment of the present invention will be described with reference to FIGS. 19 to 22.

A difference from the first and second embodiments is taking into consideration a case where the number of rotations is small in the X-ray irradiation column number n(t) calculation process (step S103 in FIG. 3), the optimal tube current I(t) calculation process (step S104 in FIG. 3), and the collimator position calculation process (step S105 in FIG. 3), that is, a range (image reconstruction range) of the image reconstruction region 200 is set to be short. Hereinafter, only differences from the first and second embodiments will be described, and description of the same parts will be omitted.

In the first and second embodiments, a description has been made of a case where collimator control in the scanning starting vicinity 60 transitions to collimator control in the scanning finishing vicinity 61 through a completely open state of the "state 4" at t=t4 illustrated in FIG. 8 with a sufficient large number of rotations. On the other hand, in a case where the number of rotations is small, an optimal tube current is calculated for an X-ray irradiation region in which both of scanning starting and scanning finishing are taken into consideration so that collimator control at the scanning starting and collimator control at the scanning finishing are taken into consideration, and thus it is possible to perform scanning with an appropriate tube current and exposure dose. Hereinafter, a description will be made of a collimator control method for creating an image while reducing ineffective exposure in the scanning starting vicinity and finishing vicinity by calculating a tube current which is the optimum for an X-ray irradiation region even in a case where the number of rotations is small, and an image reconstruction region is short.

First, an X-ray irradiation column number calculation process (step S103 in FIG. 3) will be described. FIG. 19 is a graph illustrating a temporal change in the X-ray irradiation column number n(t), in which FIG. 19(A) illustrates a case where the number of rotations is sufficiently large, and FIG. 19(B) illustrates a case where the number of rotations is small.

Figure 20:
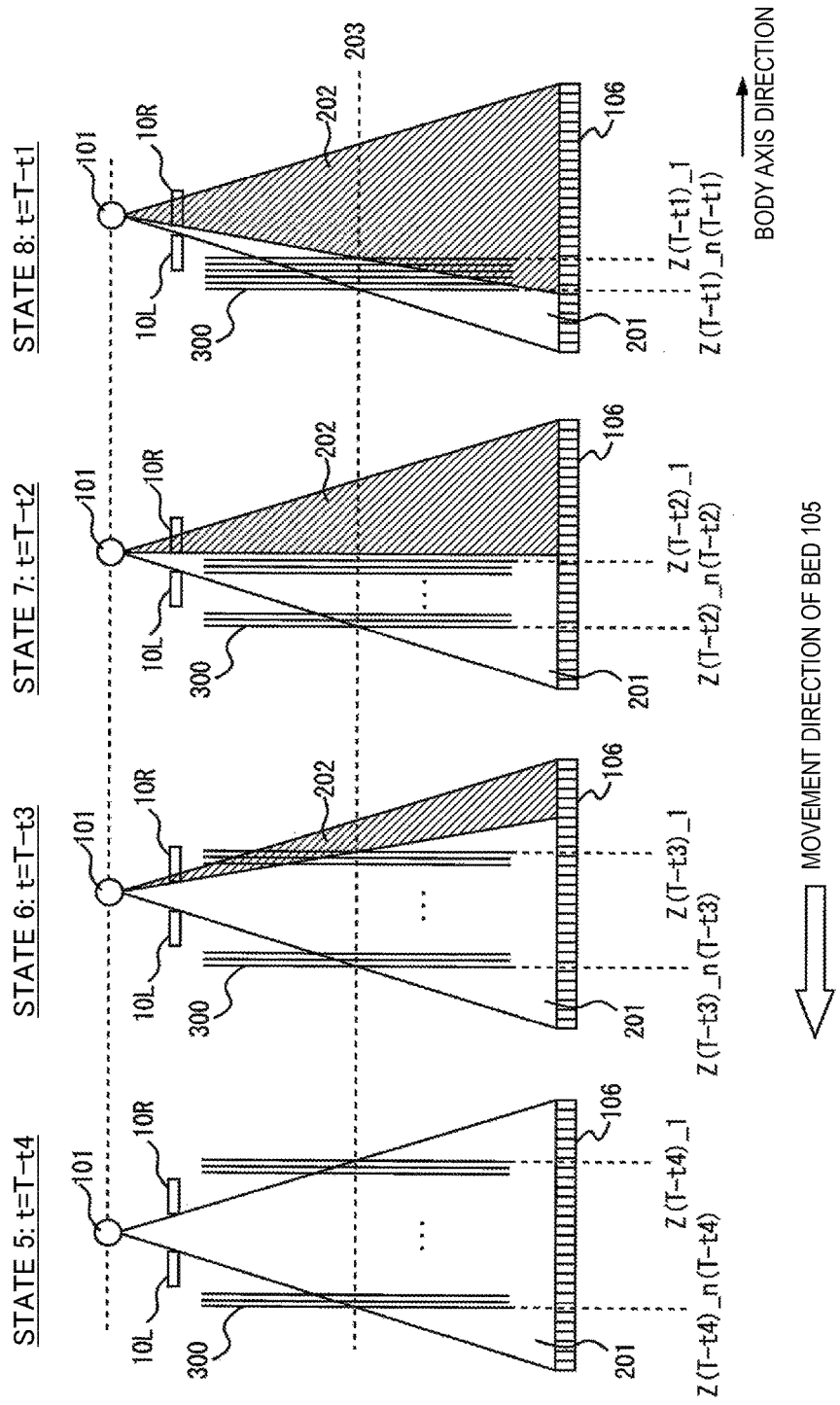
FIG. 20 is a state transition diagram of the X-ray irradiation region 201 and the analysis line 300 in the scanning finishing vicinity.

In a case where the number of rotations is sufficiently large, as illustrated in FIG. 19(A), an X-ray irradiation column number in the scanning finishing vicinity 61 may be calculated so as to be symmetrical to the scanning starting vicinity 60 through a time point t=t4 at which an X-ray irradiation column number in the scanning starting vicinity 60 increases up to the whole number of columns N, and the X-ray irradiation column number in the scanning finishing vicinity 61 decreases over time. FIG. 8 illustrates the X-ray irradiation region 201 and the X-ray shield region 202 in the scanning starting vicinity 60 over time in a case where the number of rotations is sufficiently large. FIG. 20 illustrates the X-ray irradiation region 201 and the X-ray shield region 202 in the scanning finishing vicinity 61 over time in a case where the number of rotations is sufficiently large. On the other hand, in a case where a total number of rotations T is small, T−t4 is smaller than t4 as illustrated in FIG. 19(B), and thus duration in which the scanning starting vicinity 60 overlaps the scanning finishing vicinity 61 occurs.

Here, t4 indicates a time point at which a tailing side column is necessary in order to reconstruct a leading image of the image reconstruction region 200, and T−t4 indicates a time point at which a leading side column is unnecessary in order to reconstruct a tailing image of the image reconstruction region 200. Thus, after t=T−t4, it is possible to start shielding of the leading side column which is unnecessary on the scanning starting side and the scanning finishing side. During T−t4□t<t4, an irradiation column number increasing speed on the scanning starting side is the same as an irradiation column number decreasing speed on the scanning finishing side, so as to cancel out each other, and thus a value of the X-ray irradiation column number n(t) is constant. In FIG. 19(B), this constant value is indicated as n(T/2).

Figure 21:
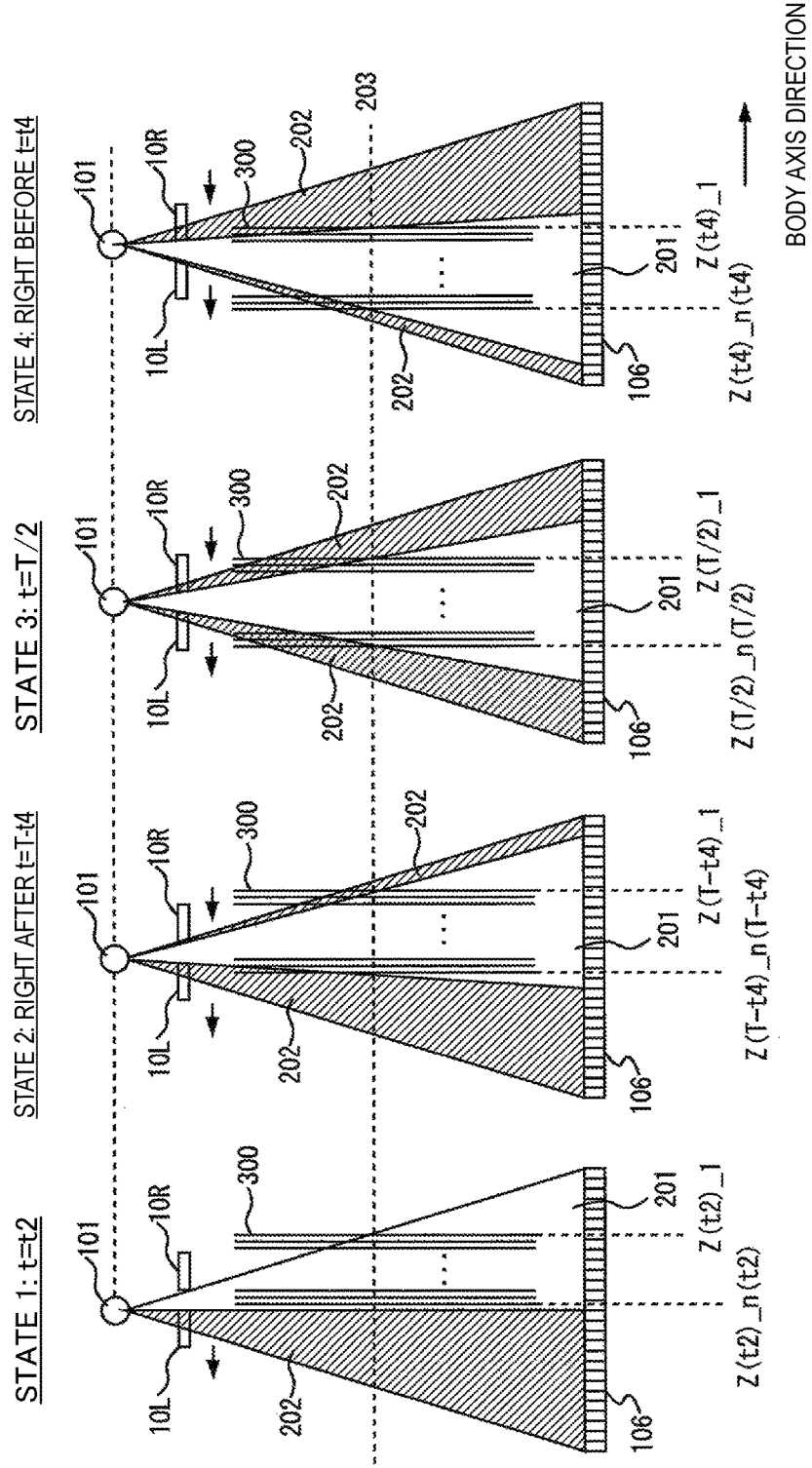
FIG. 21 is a state transition diagram of the X-ray irradiation region 201, an X-ray shield region 202, and a collimator position in a case where the number of rotations is small.

FIG. 21 is a diagram illustrating the X-ray irradiation region 201 and the X-ray shield region 202 in a case where the number of rotations is small. During a state 2 to a state 4 (T−t4≤t<t4), columns on both sides among the whole number of columns N of the X-ray detector 106 corresponding to a beam width are shielded.

If an X-ray irradiation column number required to be irradiated with X-rays after t rotations when taking into consideration image reconstruction on a leading image side is indicated by n_start(t), and an X-ray irradiation column number required to be irradiated with X-rays after t rotations when taking into consideration image reconstruction on a tailing image side is indicated by n_end(t), n_start(t) may be expressed as n(t) shown in Equations (1) and (2). In addition, n_end(t) may be expressed by Equations (29) and (30).

In the case of T−t4≤T−t2:

$$n\_end(t)=n(t2)+SOD/(SOD-FOV/2)\times HP\times (T-t2-t) \quad (29)$$

In the case of T−t2<t≤T:

$$n\_end(t)=n(t0)+SOD/(SOD-FOV/2)\times HP\times (T-t) \quad (30)$$

Since an X-ray irradiation column number during T−t4□t□t4 is expressed by the number of columns obtained by subtracting the number of unnecessary columns N−n_end(t) on the tailing image side from the number of necessary X-ray irradiation columns n_start(t) on the leading image side, the X-ray irradiation column number n(t) in a case where the number of rotations is small may be expressed by the following Equations (31), (32) and (33).

In the case of $T0 \leq t < T-t4$: (31)
$n(t) = n\_start(t)$

In the case of $T-t4 \leq t < t4$: (32)
$$n(t) = n\_start(t) - (N - n\_end(t))$$
$$= 2\times n(t2) + SOD/(SOD-FOV/2)\times HP\times (T-2\times t2) - N$$
$$= n(T/2)$$

In the case of $t4 \leq t < T$: (33)
$n(t) = n\_end(t)$

Next, a description will be made of the optimal tube current I(t) calculation process (step S104 in FIG. 3).

In a case where the number of rotations is sufficiently large, an optimal tube current is calculated as shown in step S104 on the basis of the analysis lines 300 at the slicing positions Z(t)_i (where i=1, 2, 3, . . . , and n(t)) illustrated in FIGS. 8 and 20. In a case where the number of rotations is sufficiently large, during t0≤t≤t4 in the scanning starting vicinity 60, the tailing slicing position Z(t)_n(t) changes relative to the position Z(t) of the X-ray source 101, but the leading slicing position Z(t)_1 does not change relative to Z(t). In a case where the number of rotations is sufficiently large, during T−t4≤t≤T in the scanning finishing vicinity 61, the leading slicing position Z(t)_1 changes relative to Z(t), but the tailing slicing position Z(t)_n(t) does not change relative to Z(t).

On the other hand, in a case where the number of rotations is small, an optimal tube current is calculated as shown in step S104 on the basis of the analysis lines 300 at the slicing positions Z(t)_i (where i=1, 2, 3, . . . , and n(t)) illustrated in FIG. 21. In a case where the number of rotations is small, during T−t4≤t≤t4, it is a feature that both of the leading slicing position Z(t)_1 and the tailing slicing position Z(t)_n(t) change relative to Z(t).

Next, a description will be made of the collimator position calculation process (step S105 in FIG. 3). First, in the same manner as in the first embodiment, the collimators 10 are focused in which the left collimator 10L and the right collimator 10R can be controlled separately from each other in the body axis direction during scanning. FIG. 21 illustrates a position of the left collimator 10L and the right collimator 10R. Up to t=t4, the left collimator 10L is operated in the same manner as the left collimator 10L in the scanning starting vicinity 60 in a case where the number of rotations is sufficiently large, illustrated in FIG. 8, and, after t=T−t4, the right collimator 10R is operated in the same manner as the right collimator 10R in the scanning finishing vicinity 61 in a case where the number of rotations is sufficiently large, illustrated in FIG. 20.

In a case where the number of rotations is small, the right collimator 10R in the scanning finishing vicinity does not necessarily stand still until movement of the left collimator 10L in the scanning starting vicinity is stopped. During T−t4≤t<t4, the left collimator 10L and the right collimator 10R are simultaneously appropriately moved, and thus all columns required in image reconstruction can be irradiated while minimizing exposure even in a case where the number of rotations is small.

A collimator position calculation method differs depending on a mechanism of the collimators 10.

A description will be made of a case where the collimators have a mechanism of being capable of integrally controlling a left collimator and a right collimator instead of a case where the left collimator 10L and the right collimator 10R can be separately controlled as in the above-described collimators 10.

The collimators which can be integrally controlled in the body axis direction during scanning have an aperture width between the left collimator and the right collimator. A separate pre-collimator is disposed in addition to the collimators. The pre-collimator is used to block X-rays outside a beam width.

In a case of the collimators in which the left and right collimators can be integrally controlled, X-rays are blocked by using one collimator piece of the left collimator and the right collimator so as to satisfy irradiation of at least the X-ray irradiation region 201 illustrated in FIG. 21 with X-rays.

For example, in the collimator, in order to minimize exposure, control is performed in which, up to t=T/2, the left collimator is operated to be located at the same position as the collimator position of the left collimator 10L in the scanning starting vicinity 60 illustrated in FIG. 8, at t=T/2, a collimator piece used to block X-rays instantaneously switches from the left collimator to the right collimator, and, after t=T/2, the right collimator is operated to be located at the same position as the collimator position of the right collimator 10R in the scanning finishing vicinity 61 illustrated in FIG. 20.

In the collimators which can be integrally controlled, the left and right collimators are not required to be separately from each other, and an exposure dose can be reduced with a simple structure through simple control even in a case where the number of rotations is small.

As described above, in a case where the number of rotations is small, calculation of an optimal tube current and control of the collimators are performed by taking into consideration both of the scanning starting vicinity and the scanning finishing vicinity, and thus it is possible to create a necessary image in the image reconstruction region 200 with an optimal X-ray dose while minimizing exposure in both of the collimators which can be separately controlled and of the collimators which can be integrally controlled. It is possible to achieve a sufficiently high exposure reduction effect compared with a case where scanning is performed in a state in which collimators are stationary without moving the collimators, or a case where an operation of one collimator piece is stopped and then an operation of the other collimator piece is started.

The third embodiment is useful in a case where the image reconstruction region 200 is short, such as a case of scanning a child. The third embodiment is useful in a case where an image is desired to be captured in exactly the same conditions as those of prior and posterior images when an accidental artifact or a defect occurs in a certain image during helical scanning. Third embodiment is useful in a case where an image is desired to be captured in the same conditions as those of past images since a region of a focused part is narrow, and in order to perform comparison with the past images, for example, in follow-up or a postoperative follow-up observation. A scanning condition in which a beam width is large allows wide range scanning to be performed within a short scanning period of time, and is thus a clinically preferable condition since breath holding time of an object is short. It is necessary to perform an appropriate process in a case where the number of rotations is small in order to satisfy a predetermined scanning region with a small number of rotations in the scanning condition in which a beam width is large. In the present embodiment, it is possible to perform scanning with an appropriate optimal tube current and an exposure dose even in a case where the number of rotations is small.

As mentioned above, preferred embodiments of the X-ray CT apparatus according to the present invention have been described, but the present invention is not limited to the above-described embodiments. It is clear that a person skilled in the art can conceive of various modifications or alterations within the technical spirit disclosed in the present specification, and it is understood that they are naturally included in the technical scope of the present invention.

REFERENCE SIGNS LIST

1 X-RAY CT APPARATUS, 100 SCAN GANTRY PORTION, 101 X-RAY SOURCE, 102 ROTATION BOARD, 103 COLLIMATOR UNIT, 106 X-RAY DETECTOR, 111 COLLIMATOR CONTROL DEVICE, 120 OPERATION CONSOLE, 121 INPUT DEVICE, 122 IMAGE RECONSTRUCTION DEVICE, 123 STORAGE DEVICE, 124 SYSTEM CONTROL DEVICE, 125 DISPLAY DEVICE, 130 X-RAY IRRADIATION REGION CALCULATION UNIT, 131 X-RAY DOSE CALCULATION UNIT, 132 COLLIMATOR CONTROL QUANTITY CALCULATION UNIT, 133 CONTROL UNIT, 10, 10L, AND 10R COLLIMATOR, 20 FOCAL POINT, SCANNING STARTING VICINITY, 61 SCANNING FINISHING VICINITY, 200 IMAGE RECONSTRUCTION REGION, 201 X-RAY IRRADIATION REGION, 202 X-RAY SHIELD REGION, 300 AND 320 ANALYSIS LINE

The invention claimed is:

1. An X-ray CT apparatus comprising:
an X-ray source that irradiates an object with X-rays;
a collimator that restricts an irradiation range of the X-rays applied from the X-ray source;
an X-ray detector that is disposed to oppose the X-ray source and detects X-rays having been transmitted through the object;
a rotation board that is mounted with the X-ray source and the X-ray detector and is rotated around the object;
a bed that carries the object into and out of an X-ray irradiation region;
an image reconstruction device that reconstructs an image of the object on the basis of a transmitted X-ray dose detected by the X-ray detector;
a display device that displays the image reconstructed by the image reconstruction device;
an X-ray irradiation region calculation unit that calculates an X-ray irradiation region in a body axis direction at each view angle on the basis of an examination condition;
an X-ray dose calculation unit that calculates an irradiation X-ray dose at each view angle according to an X-ray irradiation region calculated by the X-ray irradiation region calculation unit; and
a control unit that controls scanning so that the irradiation X-ray dose calculated by the X-ray dose calculation unit is applied to the X-ray irradiation region at each view angle calculated by the X-ray irradiation region calculation unit;
wherein the X-ray irradiation region includes a position deviated in the body axis direction relative to a position of the X-ray source, and
wherein the X-ray dose calculation unit sets an analysis line for determining the irradiation X-ray dose in the X-ray irradiation region, and calculates the irradiation X-ray dose on the basis of an analysis result in the set analysis line.

2. The X-ray CT apparatus according to claim 1, wherein the analysis line is set to be perpendicular to the body axis direction.

3. The X-ray CT apparatus according to claim 1, wherein the analysis line is set according to an incidence angle of an X-ray at each position in the X-ray irradiation region.

4. The X-ray CT apparatus according to claim 1,
wherein the X-ray dose calculation unit sets a plurality of analysis lines in the X-ray irradiation region at each view angle, calculates candidates of irradiation X-ray doses for each analysis line, and uses any one of an average value, the maximum value, and the minimum value of the calculated candidates of X-ray doses as an irradiation X-ray dose at the view angle.

5. The X-ray CT apparatus according to claim 1,
wherein the X-ray dose calculation unit sets the analysis line at a representative slicing position in the X-ray irradiation region at each view angle, calculates an irradiation X-ray dose in the set analysis line, and uses the calculated irradiation X-ray dose as an irradiation X-ray dose at the view angle.

6. The X-ray CT apparatus according to claim 1,
wherein the X-ray irradiation region calculation unit and the X-ray dose calculation unit perform calculation of the X-ray irradiation region and calculation of the irradiation X-ray dose in either one or both of the scanning starting vicinity and the scanning finishing vicinity during helical scanning.

7. An X-ray CT apparatus comprising:
an X-ray source that irradiates an object with X-rays;
a collimator that restricts an irradiation range of the X-rays applied from the X-ray source;
an X-ray detector that is disposed to oppose the X-ray source and detects X-rays having been transmitted through the object;
a rotation board that is mounted with the X-ray source and the X-ray detector and is rotated around the object;
a bed that carries the object into and out of an X-ray irradiation region;
an image reconstruction device that reconstructs an image of the object on the basis of a transmitted X-ray dose detected by the X-ray detector;
a display device that displays the image reconstructed by the image reconstruction device;
an X-ray irradiation region calculation unit that calculates an X-ray irradiation region in a body axis direction at each view angle on the basis of an examination condition;
an X-ray dose calculation unit that calculates an irradiation X-ray dose at each view angle according to an X-ray irradiation region calculated by the X-ray irradiation region calculation unit; and
a control unit that controls scanning so that the irradiation X-ray dose calculated by the X-ray dose calculation unit is applied to the X-ray irradiation region at each view angle calculated by the X-ray irradiation region calculation unit;
wherein the X-ray irradiation region calculation unit calculates the X-ray irradiation region on the basis of an image reconstruction condition in the examination condition.

8. The X-ray CT apparatus according to claim 7, further comprising:
an examination condition setting unit that sets a post-reconstruction condition which is different from a reconstruction condition for image reconstruction performed during scanning, as the examination condition,
wherein the X-ray irradiation region calculation unit calculates the X-ray irradiation region on the basis of the reconstruction condition during scanning and the post-reconstruction condition.

9. The X-ray CT apparatus according to claim 7, further comprising:
a collimator control unit that controls the collimator so that the X-ray irradiation region is irradiated with an umbra of X-rays according to a change in each view angle of the X-ray irradiation region calculated by the X-ray irradiation region calculation unit.

10. The X-ray CT apparatus according to claim 9,
wherein the collimator control unit further controls the collimator on the basis of parameters including one or more of a focal point size of the X-ray source, a thickness of the collimator, and a channel direction open angle of X-rays incident to the X-ray detector.

11. The X-ray CT apparatus according to claim 9,
Wherein, in a case where the collimator includes a plurality of collimator pieces, the collimator control unit further simultaneously controls the plurality of collimator pieces on the basis of the number of rotations or a set image reconstruction range in the examination condition.

12. The X-ray CT apparatus according to claim 9, further comprising:
an exposure dose calculation unit that calculates an exposure dose on the basis of a collimator position calculated by the collimator control unit and an irradiation X-ray dose calculated by the X-ray dose calculation unit; and
a user interface unit that displays, on the display device, one or more of a temporal change of the X-ray irradiation region, a slicing position change of the X-ray irradiation region, a temporal change of the irradiation X-ray dose, a slicing position change of the irradiation X-ray dose, a temporal change of the exposure dose, and a slicing position change of the exposure dose.

13. The X-ray CT apparatus according to claim 7,
wherein the X-ray irradiation region calculation unit calculates the X-ray irradiation region, and the X-ray dose calculation unit calculates the irradiation X-ray dose, by taking into consideration both of the scanning starting vicinity and the scanning finishing vicinity during helical scanning on the basis of the number of rotations or an image reconstruction range in the examination condition.

14. An X-ray CT apparatus comprising:
an X-ray source that irradiates an object with X-rays;
a collimator that restricts an irradiation range of the X-rays applied from the X-ray source;
an X-ray detector that is disposed to oppose the X-ray source and detects X-rays having been transmitted through the object;
a rotation board that is mounted with the X-ray source and the X-ray detector and is rotated around the object;
a bed that carries the object into and out of an X-ray irradiation region;
an image reconstruction device that reconstructs an image of the object on the basis of a transmitted X-ray dose detected by the X-ray detector;
a display device that displays the image reconstructed by the image reconstruction device;
an X-ray irradiation region calculation unit that calculates an X-ray irradiation region in a body axis direction at each view angle on the basis of an examination condition;
an X-ray dose calculation unit that calculates an irradiation X-ray dose at each view angle according to an X-ray irradiation region calculated by the X-ray irradiation region calculation unit;
a control unit that controls scanning so that the irradiation X-ray dose calculated by the X-ray dose calculation unit is applied to the X-ray irradiation region at each view angle calculated by the X-ray irradiation region calculation unit;

an exposure dose calculation unit that calculates an exposure dose on the basis of an X-ray irradiation region calculated by the X-ray irradiation region calculation unit and an irradiation X-ray dose calculated by the X-ray dose calculation unit; and a user interface unit that displays, on the display device, one or more of a temporal change of the X-ray irradiation region, a slicing position change of the X-ray irradiation region, a temporal change of the irradiation X-ray dose, a slicing position change of the irradiation X-ray dose, a temporal change of the exposure dose, and a slicing position change of the exposure dose.

15. The X-ray CT apparatus according to claim 14, further comprising:

an exposure range calculation unit that calculates an exposure range on the basis of the X-ray irradiation region calculated by the X-ray irradiation region calculation unit, wherein the user interface unit displays a temporal change of the exposure range or a slicing position change of the exposure range.

16. The X-ray CT apparatus according to claim 14, wherein the user interface unit displays a temporal change or a slicing position change of an irradiation X-ray dose calculated by the X-ray dose calculation unit, and a temporal change or a slicing position change of an irradiation X-ray dose calculated at a slicing position of the X-ray source for comparison therebetween.

17. The X-ray CT apparatus according to claim 14, further comprising:

an input unit that inputs an instruction for permitting or not permitting scanning according to the display content in the user interface unit, wherein the control unit starts scanning if an instruction for permitting scanning is input via the input unit, and transitions to resetting of the examination condition if an instruction for not permitting scanning is input via the input unit.

* * * * *